US006461811B1

(12) United States Patent
Patience

(10) Patent No.: US 6,461,811 B1
(45) Date of Patent: Oct. 8, 2002

(54) GAMMA-HERPES VIRUS DNA AND METHODS OF USE

(75) Inventor: Clive Patience, Beverly, MA (US)

(73) Assignee: BioTransplant, Inc., Charlestown, MA (US)

( * ) Notice: Subject to any disclaimer, the term of this patent is extended or adjusted under 35 U.S.C. 154(b) by 0 days.

(21) Appl. No.: 09/612,204

(22) Filed: Jul. 7, 2000

Related U.S. Application Data

(60) Provisional application No. 60/168,532, filed on Dec. 2, 1999, and provisional application No. 60/142,736, filed on Jul. 8, 1999.

(51) Int. Cl.[7] ............................ C12Q 1/70; C12Q 1/68; C12P 19/30; C12N 15/00

(52) U.S. Cl. .............................. 435/5; 435/6; 435/7.21; 435/69.3; 435/320.1; 536/23.1; 536/23.72; 536/24.3; 536/24.31

(58) Field of Search ............................... 536/23.1, 23.5, 536/24.31, 24.3, 4.32, 23.72; 435/5, 6, 7.21, 69.1, 69.3, 320.1

(56) References Cited

PUBLICATIONS

Pharmacia BioDirectory catalog. 1996. p. 225.*

Simas, et al., "Murine gammaherpesvirus 68: a model for the study of gammaherpesvirus pathogenesis," Trends in Microbiology, vol. 6, No. 7, pp. 276–282 (Ju. 1998).

Bahr, et al., "Structural organization of a conserved gene cluster of Tupaia herpesvirus encoding the DNA polymerase, glycoprotein B, a probable processing and transport protein, and the major DNA binding protein," Virus Research, pp. 123–136 (1999).

Ehlers, et al., "Detection of two novel porcine herpesviruses with high similarity to gammaherpesviruses," Journal of General Virology, pp. 971–978 (1999).

Ulrich, et al., "Characterization of the DNA polymerase loci of the novel porcine lymphotropic herpesviruses 1 and 2 in domestic and feral pigs," pp. 3199–3205 (1999).

Morozov, et al., "Detection of a Novel Strain of Porcine Circovirus in Pigs with Postweaning Multisystemic Wasting Syndrome," vol. 36, No. 9, pp. 2535–2541 (Sep. 1998).

* cited by examiner

*Primary Examiner*—Laurie Scheiner
*Assistant Examiner*—Shanon A. Foley
(74) *Attorney, Agent, or Firm*—Elliot M. Olstein; Alan J. Grant

(57) ABSTRACT

Isolated polynucleotides and polypeptides derived from the genome of swine gamma-herpesviruses are disclosed, including recombinant cells and vectors encoding such polypeptides and expressing such polynucleotides. Use of the novel polynucleotides as probes of the swine genome is also described. Assay methods employing antibodies against the isolated polypeptides are also disclosed.

25 Claims, 14 Drawing Sheets

Figure 1(a)

```
HHV8PEP         -----------------------MTPRSR-LATLGTVILLVCFCAG--AAHSRGDTFQ--
RHESRHADPEP     ---------------------MMITNRTRRLLRAWVVIIAIGTAVG--ENVTTPKGAT--
MURH68PEP       ---------------------MYPTVKSMRVAHLTNLLTLLCLLCHTHLYVCQPTTLR--
BOVINEH4PEP     YYKTILFFALIKVCSFNQTTTHSTTTSPSISSTTSSTTTSTSKPSNTTSTNSSLAASPQ
ATELINEH3PEP    ------------------------MTLNR---CVLLIVLTFSTACS-----------Q--
SAIMIRIPEP      ------------------------MVPNK---HLLLIILSFSTACG-----------Q--
EQH2PEP         ---------------------MGVGGGPRVVLCLWCVAALLCQGVAQEVVAETTTPFA--
EQH5PEP         ---------------------MVAWFGLWGFARLMATLALLCGRVALDESSATPSIPP--
ALCELPEP        --------------------MAHTGSTVCAFLIFAVLKNVFCQTPTSSSEVEDVIPEAN-
EBVPEP          ------------------------MTRRRVLSVVVLLAALACRLGA-----Q--TPEQ--

HHV8PEP         --TSSSPTPPGSSSKAPTKPGEEASGPKSVDFYQFRVCSAS-ITGELFRFNLEQTCPDTK
RHESRHADPEP     --TTAKPTP-GPS--TPTPP---ENPPR-AEAFKFRVCSAS-ATGELFRFNLEKTCPGTE
MURH68PEP       --QPSDMTP-AQDAPTETPPPLSTNTNR--GFEYFRVCGVA-ATGETFRFDLDKTCPSTQ
BOVINEH4PEP     NTSTSKPSTDNQGTSTPTIPTVTDDTAS-KNFYKYRVCSASSSSGELFRFDLDQTCPDTK
ATELINEH3PEP    ----TTPASSDEN--GKTPAIEK--EYF----K-YRVCSAS-TTGELFRFNLDRACPSTE
SAIMIRIPEP      ----TTPTTAVEK--NKTQAIYQ--EYF----K-YRVCSAS-TTGELFRFDLDRTCPSTE
EQH2PEP         ---THRPEVVAEE--NPANP-----FLP----F--RVCGASPTGGEIFRFPLEESCPNTE
EQH5PEP         ---THKPAVHHED--NTTNP-----FLL----F--RVCGASPTG-EIFRFPLEENCPNTE
ALCELPEP        --TVSDNIIRQQR--NNTAKGIHSDPSA----FPFRVCSAS-NIGDIFRFQTSHSCPNTK
EBVPEP          ---PAPPATTVQP--TATRQ-----QTS----FPFRVCELS-SHGDLFRFSSDIQCPSFG

HHV8PEP         DKY-HQEGILLVYKKNIVPHIFKVRRYRKIATSVTVYRGLTES--AITNKYELPRPVPLY
RHESRHADPEP     DKT-HQEGILMVFKKNIVPHIFKVRRYRKVATSVTVYRGWTET--AVTGKQEVIRPVPQY
MURH68PEP       DKK-HVEGILLVYKINIVPYIFKIRRYRKIITQLTIWRGLTTS--SVTGKFEMATQAHEW
BOVINEH4PEP     DKK-HVEGILLVLKKNIVPYIFKVRKYRKIATSVTVYRGWSQA--AVTNRDDISRAIPYN
ATELINEH3PEP    DKV-HREGILLVYKKNIVPHIFKVRRYKKIATSVRIFNGWSREGVAITNKWELSRAVPKY
SAIMIRIPEP      DKV-HKEGILLVYKKNIVPYIFKVRRYKKITTSVRIFNGWTREGVAITNKWELSRAVPKY
EQH2PEP         DKD-HIEGIALIYKTNIVPYVFNVRKYRKIMTSTTIYKGWSED--AITNQHTRSYAVPLY
EQH5PEP         DKE-HVEGILLIYKTNIVPYIFNVRKYRKLVTSTTIYKGWSQD--AITNQYTSSFAMPLW
ALCELPEP        DKE-HNEGILLIFKENIVPYVFKVRKYRKIVTTSTIYNGIYAD--AVTNQHVFSKSVPIY
EBVPEP          TRENHTEGLLMVFKDNIIPYSFKVRSYTKIVTNILIYNGWYAD--SVTNRHEEKFSVDSY

HHV8PEP         EISHMDSTYQCFSSMKVNVNGVENTFTDRDDVNTTVFLQPVEGLTDNIQRYFSQPVIYAE
RHESRHADPEP     EINHMDTTYQCFSSMRVNVNGIVNTYTDRDFTNQTVFLQPVEGLTDNIQRYFSQPVLYTT
MURH68PEP       EVGDFDSIYQCYNSATMVVNNVRQVYVDRDGVNKTVNIRPVDGLTGNIQRYFSQPTLYSE
BOVINEH4PEP     EISMIDRTYHCFSAMATVINGILNTYIDRDSENKSVPLQPVAGLTENINRYFSQPLIYAE
ATELINEH3PEP    EINLMDKNYQCHNCMQIEVNGLLNSYCDRDGNNKTVDLKPVDGLTGAITRYVSQPKIFAD
SAIMIRIPEP      EIDIMDKTYQCHNCMQIEVNGMLNSYYDRDGNNKTVDLKPVDGLTGAITRYISQPKVFAD
EQH2PEP         EVQMMDHYYQCFSAVQVNEGGHVNTYYDRDGWNETAFLKPADGLTSSITRYQSQPEVYAT
EQH5PEP         EARLVDYNYECYNGIQVTENGHLTTYVDRDGYNESVRLVPADGLTSSIRRYHSQPELYVT
ALCELPEP        ETRRMDTIYQCYNSLDVTVGGNLLVYTDNDGSNMTVDLQPVDGLSNSVRRYHSQPEIHAE
EBVPEP          ETDQMDTIYQCYNAVKMTKDGLTRVYVDRDGVNITVNLKPTGGLANGVRRYASQTELYDA

HHV8PEP         PGWFPGIYRVRTTVNCEIVDMIARSAEPYNYFVTSLGDTVEVSPFCYNESSCST-TPSNK
RHESRHADPEP     PGWFPGIYRVRTTVNCEIVDMIARSAEPYSYFVTALGDTVEVSPFCHNDSTCSV-AEKTE
MURH68PEP       PGWMPGFYRVRTTVNCEIVDMVARSMDPYNYIATALGDSLELSPFQTFDNTSQS-TAPKR
BOVINEH4PEP     PGWFPGIYRVRTTVNCEVVDMYARSVEPYTHFITALGDTIEISPFCHNNSQCTTGNSTSR
ATELINEH3PEP    AGWLWGTYKTRTTVNCEIVEMFARSADPYTYFVTALGDTVEVSPFCDAENSCPN----AS
SAIMIRIPEP      PGWLWGTYRTRTTVNCEIVDMFARSADPYTYFVTALGDTVEVSPFCDVDNSCPN----AT
EQH2PEP         PRNLLWSYTTRTTVNCEVTEMSARSMKPFEFFVTSVGDTIEMSPFLKENGTEPE--KILK
EQH5PEP         PRNLLWSYTTRTTVNCEVIDMTARSHKPFEYFVTASGDSIETSPFYT-NASR-------R
ALCELPEP        PGWLLGGYRRRTTVNCEVTETDARAVPPFRYFITNIGDTIEMSPFWSKAWNETEFS--GE
EBVPEP          PGWLIWTYRTRTTVNCLITDMMAKSNSPFDFFVTTTGQTVEMSPFYDGKNKETF----HE
```

Figure 1(b)

| | |
|---|---|
| HHV8PEP | NGLSVQVVLNHTVVTYSDRGTSPTPQNRIFVETGAYTLSWASESKTTAVCPLALWKTFPR |
| RHESRHADPEP | NGLGARVLTNYTMVDFATR--APTTETRVFADSGEYTVSWKAEDPKSAVCALTLWKTFPR |
| MURH68PEP | ADMRVREVKNYKFVDYNNRGTAPAGQSRTFLETPSATYSWKTATRQTATCDLVHWKTFPR |
| BOVINEH4PEP | DATKVWIEENHQTVDYERRG-HPTKDKRIFLKDEEYTISWKAEDRERAICDFVIWKTFPR |
| ATELINEH3PEP | DVLSSQVDFNHTVVDYGNRATSQQHGKRIFAHTLDYSVSWEAINKTTSVCSMVFWKGFQR |
| SAIMIRIPEP | DVLSVQIDLNHTVVDYGNRATSQQHKKRIFAHTLDYSVSWEAVNKSASVCSMVFWKSFQR |
| EQH2PEP | RPHSIQLLKNYAVTKYGVGLGQADNATRFFAIFGDYSLSWKATTENSSYCDLILWKGFSN |
| EQH5PEP | VP--VQVLYNYSVTDYGVGLGSGENVTRFFATLNDFSISWKAATENSSYCPLVLWKGFPS |
| ALCELPEP | PDRTLTVAKDYRVVDYKFRGTQPQGHTRIFVDKEEYTLSWAQQFRNISYCRWAHWKSFDN |
| EBVPEP | RADSFHVRTNYKIVDYDNRGTNPQGERRAFLDKGTYTLSWKLENR-TAYCPLQHWQTFDS |

| | |
|---|---|
| HHV8PEP | SIQTTHEDSFHFVANEITATFTAP---LTPVANFTDTYSCLTSDINTTLNASKAKLASTH |
| RHESRHADPEP | AIQTTHEASYHFVANDVTATFTSP---LSEVANFTGTYSCLDEVIQKTLNDTIKKLSDTH |
| MURH68PEP | AIQTAHEHSYHFVANEVTATFNTP---LTEVENFTSTYSCVSDQINKTISEYIQKLNNSY |
| BOVINEH4PEP | AIQTIHNESFHFVANEVTASFLTSNQEETELRGNTEILNCMNSTINETLEETVKKFNKSH |
| ATELINEH3PEP | AIQTEHDSTYHFIANEITAGFSTS---KETLASFSSEYSCLMSDINSTLTDKIGRVNNTH |
| SAIMIRIPEP | AIQTEHDLTYHFIANEITAGFSTV---KEPLANFTSDYNCLMTHINTTLEDKIARVNNTH |
| EQH2PEP | AIQTQHNSSLHFIANDITASFSTP--LEEEAN-FNETFKCIWNNTQEEIQKKLKEVEKTH |
| EQH5PEP | AIQTKHEKSYHFIADAVTASFTTP--LTDETSYFNTTYQCAWQDIEGEIQKRFDPVSKTH |
| ALCELPEP | AIKTEHGKSLHFVANDITASFYTP---NTQTREVLGKHVCLNNTIESELKSRLAKVNDTH |
| EBVPEP | TIATETGKSIHFVTDEGTSSFVTN---TTVGIELPDAFKCIEEQVNKTMHEKYEAVQDRY |

| | |
|---|---|
| HHV8PEP | VP-NGTVQYFHTTGGLYLVWQPMSAINLTHAQ-GDSGNPTSSPPPSASP----------M |
| RHESRHADPEP | VT-NGSAQYYKTEGGLFLLWQPLTPLSLVDEMRGLNG---TTPAP---P----------A |
| MURH68PEP | VA-SGKTQYFKTDGNLYLIWQPLEHPEIEDID--EDSDPEPTPAP---P----------K |
| BOVINEH4PEP | IR-DGEVKYYKTNGGLFLIWQAMKPLNLSEHT------N-YTIER---N----------N |
| ATELINEH3PEP | VP-NGTAQYFKTEGGMILVWQPLTAIELEEAMIEATTVSPTPLS---------------T |
| SAIMIRIPEP | TP-NGTAEYYQTEGGMILVWQPLIAIELEEAMLEATTSPVTPSAP--------------T |
| EQH2PEP | RP-NGTAKVYKTTGNLYIVWQPLIQIDLLDTHAKLYNLTNATASPTSTP----------- |
| EQH5PEP | AR-NGSVQIYKTSGNLYVVWQPLVQLDLLAAHAKTINSTDNSTSPTTAPN--------TT |
| ALCELPEP | SP-NGTAQYYLTNGGLLLVWQPLVQQKLLDAKGLLDAVKKQQNTTTT------------T |
| EBVPEP | TKGQEAITYFITSGGLLLAWLPLTPRSLATVKNLTELTTPTSSPPSSPSPPAPSAARGST |

| | |
|---|---|
| HHV8PEP | TTSASRRKRRSASTAAAGG---GGSTDN-----LSYT**QLQFAYDKL**RDGINQVLEELSRA |
| RHESRHADPEP | TTSTVSRVRRSVNTNEQ-------ATDN-----LAAP**QLQFAYDKL**RASINKVLEELSRA |
| MURH68PEP | STRRKREAADNGNSTSEVS---KGSENP-----LITA**QIQFAYDKL**TTSVNNVLEELSRA |
| BOVINEH4PEP | KTGNKSRQKRSVDTKTFQG-----AKG------LSTA**QVQYAYDHL**RTSMNHILEELTKT |
| ATELINEH3PEP | AHLTSRRTGRRKRDVSAG------SENS-----VLLA**QIQYAYDKL**RQSINNVLEELAIT |
| SAIMIRIPEP | SSSRSKRAIRSIRDVSAG------SENN-----VFLS**QIQYAYDKL**RQSINNVLEELAIT |
| EQH2PEP | -TTSPRRRRRDTSSVSGGG---NNGDNSTKEESVAAS**QVQFAYDNL**RKSINRVLGELSRA |
| EQH5PEP | TSTSSRRKRRDTGNTATNN---SSSNNSSMEENLATS**QVQFAYDQL**RKSINRVLEQLSRV |
| ALCELPEP | TTTRSRRQRRSVSSGIDDV---YTAEST-----ILLT**QIQFAYDTL**RAQINNVLEELSRA |
| EBVPEP | PAAVLRRRRRDAGNATTPVPPTAPGKSLGTLNNPATV**QIQFAYDSL**RRQINRMLGDLARA |

| | |
|---|---|
| HHV8PEP | WCREQVRDNLMWY**ELSKINPTSVMTAIYGRP**VSAKFVGDAISVTECINVDQSSVNIHKSL |
| RHESRHADPEP | WCREQVRDTYMWY**ELSKINPTSVMTAIYGRP**VSAKFVGDAISVTDCVAVDQASVSIHKSL |
| MURH68PEP | WCREQVRDTLMWY**ELSKVNPTSVMSAIYGKP**VAARYVGDAISVTDCIYVDQSSVNIHQSL |
| BOVINEH4PEP | WCREQKKDNLMWY**ELSKINPVSVMAAIYGKP**VAVKAMGDAFMVSECINVDQASVNIHKSM |
| ATELINEH3PEP | WCREQVRQTMIWY**EIAKINPTSVMTAIYGKP**VSAKALGDVISVTECINVDQTSVSIHKSL |
| SAIMIRIPEP | WCREQVRQTMVWY**EIAKINPTSVMTAIYGKP**VSRKALGDVISVTECINVDQSSVSIHKSL |
| EQH2PEP | WCREQYRASLMWY**ELSKINPTSVMSAIYGRP**VSAKLIGDVVSVSDCISVDQKSVFVHKNM |
| EQH5PEP | WCQNQYRASLMWY**ELSKINPTSVMSAIYGRP**VSAKLVGDVVQISDCITVDQESVFVHRNL |
| ALCELPEP | WCREQHRASLMWN**ELSKINPTSVMSSIYGRP**VSAKRIGDVISVSHCVVVDQDSVSLHRSM |
| EBVPEP | WCLEQKRQNMVLR**ELTKINPTTVMSSIYGKA**VAAKRLGDVISVSQCVPVNQATVTLRKSM |

Figure 1(c)

```
HHV8PEP        RTN---SKDVCYARPLVTFKFLNSSNLFTGQLGARNEIILTNNQVETCKDTCEHYFITRN
RHESRHADPEP    RTS---TPGMCYSRPPVTFRFLNSTTLFKGQLGPRNEIILTDNQVEACKETCEHYFIASN
MURH68PEP      RLQH--DKTTCYSRPRVTFKFINSTDPLTGQLGPRKEIILSNTNIETCKDESEHYFIVGE
BOVINEH4PEP    RTD---DPKVCYSRPLVTFKFVNSTATFRGQLGTRNEILLTNTHVETCRPTADHYFFVKN
ATELINEH3PEP   KTT---NNDVCYSRPPVTFKFVNSSQLFKGQLGARNEILLSESLVENCHQNAEHFFTAKN
SAIMIRIPEP     KTE---NNDICYSRPPVTFKFVNSSQLFKGQLGARNEILLSESLVENCHQNAETFFTAKN
EQH2PEP        KVPG--KEDLCYTRPVVGFKFINGSELFAGQLGPRNEIVLSTSQVEVCQHSCEHYFQAGN
EQH5PEP        RVPG--SKDLCYTRPVVGFKFINGSELFVGQLGARNEILLSTNLVEVCQHSCEHYFQGGN
ALCELPEP       RVPGRDKTHECYSRPPVTFKFINDSHLYKGQLGVNNEILLTTTAVEICHENTEHYFQGGN
EBVPEP         RVPG--SETMCYSRPLVSFSFINDTKTYEGQLGTDNEIFLTKKMTEVCQATSQYYFQSGN

HHV8PEP        ETLVYKDYAYLRTINTTDISTLNTFIALNLSFIQNIDFKAIELYSSAEKRLASSVFDLET
RHESRHADPEP    VTYYYKDYVFVKKINTSEISTLGTFIALNLSFIENIDFRVIELYSRAEKKLSGSVFDIET
MURH68PEP      YIYYYKNYIFEEKLNLSSIATLDTFIALNISFIENIDFKTVELYSSTERKLASSVFDIES
BOVINEH4PEP    MTHYFKDYKFVKTMDTNNISTLDTFLTLNLTFIDNIDFKTVELYSETERKMAS-ALDLET
ATELINEH3PEP   ETYHFKNYLHVETLPLTNISTLDTFLALNLTFIENIDFKAVELYSSGERKLAN-VFDLET
SAIMIRIPEP     ETYHFKNYVHVETLPVNNISTLDTFLALNLTFIENIDFKAVELYSSGERKLAN-VFDLET
EQH2PEP        QMYKYKDYYYVSTLNLTDIPTLHTMITLNLSLVENIDFKVIELYSKTEKRLSN-VFDIET
EQH5PEP        HIYKYKNYEYVSTMNLTDVPTLHTMITLNLSLVENVDFQVIQLYSQKEKKLSN-VFDIET
ALCELPEP       NMYFYKNYRHVKTMPVGDVATLDTFMVLNLTLVENIDFQVIELYSREEKRMST-AFDIET
EBVPEP         EIHVYNDYHHFKTIELDGIATLQTFISLNTSLIENIDFASLELYSRDEQRASN-VFDLEG

HHV8PEP        MFREYNYYTHRLAGLREDLDNTIDMNKERFVRDLSEIVADLGGIGKTVVNVASSVVTLCG
RHESRHADPEP    MFREYNYYTQRLAGLREDLDNTIDLNRDRLARDLSEIVADLGDVGRTVVNVASSVITLFG
MURH68PEP      MFREYNYYTYSLAGIKKDLDNTIDYNRDRLVQDLSDMMADLGDIGRSVVNVVSSVVTFFS
BOVINEH4PEP    MFREYNYYTQKLASLREDLDNTIDLNRDRLVKDLSEMMADLGDIGKVVVNTFSGIVTVFG
ATELINEH3PEP   MFREYNYYAQSISGLRKDFDNSQRNNRDRIIQDFSEILADLGSIGKVIVNIASSAFSLFG
SAIMIRIPEP     MFREYNYYAQSISGLRKDFDNSQRNNRDRIIQDFSEILADLGSIGKVIVNVASGAFSLFG
EQH2PEP        MFREYNYYTQNLNGLRKDLDDSIDHGRDSFIQTLGDIMQDLGTIGKVVVNVASGVFSLFG
EQH5PEP        MFREYNYYTQNLKGLRKDLDDSIHDGRDSFIQFLGDLVQDLVPVGDVIVNVASGVFSLFG
ALCELPEP       MFREYNYYTQRVTGLRRDLTD-LATNRNQFVDAFGSLMDDLGVVGKTVLNAVSSVATLFS
EBVPEP         IFREYNFQAQNIAGLRKDLDNAVSNGRNQFVDGLGELMDSLGSVGQSITNLVSTVGGLFS

HHV8PEP        SLVTGFINFIKHPLGGMLMIIIVIAIILIIFMLSRRTNTIAQAPVKMIYP----DVDRRA
RHESRHADPEP    SIVSGFINFIKSPFGGMLMILVIVAVVLIVFALNRRTNAIAQAPIRMIYP----DIDKMQ
MURH68PEP      SIVTGFIKFFTNPLGGIFILLIIGGIIFLVVVLNRRNSQFHDAPIKMLYPSVENYAARQA
BOVINEH4PEP    SIVGGFVSFFTNPIGGVTIILLLIVVVFVVFIVSRRTNNMNEAPIKMIYP----NIDKAS
ATELINEH3PEP   GIVTGILNFIKNPLGGMLTFLLVGAIIILVILLVRRTNNMSQAPIRMIYP----DIEKSR
SAIMIRIPEP     GIVTGILNFIKNPLGGMFTFLLIGAVIILVILLVRRTNNMSQAPIRMIYP----DVEKSK
EQH2PEP        SIVSGVISFFKNPFGGMLLIVLIIAGVVVVYLFMTRSRSIYSAPIRMLYP----GVERAA
EQH5PEP        SIVSGVISFLKNPLGAILTIALIVGGIIVLYLFITRSRTVYQAPIRMLYP----EVDRAP
ALCELPEP       SIVSGIINFIKNPFGGMLLFGLIAAVVITVILLNRKAKRFAQNPVQMIYP----DIKTIT
EBVPEP         SLVSGFISFFKNPFGGMLILVLVAGVVILVISLTRRTRQMSQQPVQMLYP----GIDELA

HHV8PEP        PP-------SGGAPTREEIKNILLGMHQLQQ----ERQKADDLKKSTPSVFQRTANGLR
RHESRHADPEP    P--------SGGKVDQEQIKNILAGMHQLQQ----EERRRLDEQQRSAPSLFRRASDGLK
MURH68PEP      PPPYSA---SPPAIDKEEIKRILLGMHQVHQ----EEKEAQKQLTNSGPTLWQKATGFLR
BOVINEH4PEP    EQE------NIQPLPGEEIKRILLGMHQLQQ----SEHGKSEEEASHKPGLFQLLGDGLQ
ATELINEH3PEP   S--------SVTPTEPEVIKQILLGMHNMQQ----EEYKKREEHKASQPSFLKRATDAFL
SAIMIRIPEP     S--------TVTPMEPETIKQILLGMHNMQQ----EAYKKKEEQRAARPSIFRQAAETFL
EQH2PEP        QEP------GAHPVSEDQIRNILMGMHQFQQRQRAEEEARREEEVKGKRTLFEVIRDSAT
EQH5PEP        QQ-------NVQPIPEDQVRSILLAMHQFQQQQQQQQQQQQEEHTQ-RRSIFDTIRESTS
ALCELPEP       SQREEL---QVDPISKHELDRIMLAMHDYHASK--QPESKQDEEQGSTTSGPADWLNKAK
EBVPEP         QQHASGEGPGINPISKTELQAIMLALHEQNQ------EQKRAAQRAAGPSVASRALQAAR
```

Figure 2

```
ATGGCAGGTA GCTTAAAACT TAGGGGATCT GTTCTAGCAC TGTGGTACCT GTATCAGGTG 60
GCTCTTTATT CACTTAGTAT AGCAGAGACC GGTGTAACCT CACCTCCAAA TACAGCGACC 120
TGGTCTACTG AATCGCCGCT AACAGGTCAC TATGGAACAC ACGATTCAAG CCATGGTGAA 180
AGAGGAAACA ACGAAAACAG AGATTCAGAA GAGCAAAATA AAAACATTTA TGGATCGCCT 240
TCTACGTTTC CTTACAGAGT ATGCAGTGCC TCCGGAGTTG GAGATGTCTT TAGATTTCAG 300
ACCGACCATG TGTGTCCCGA TGCCAGTGAT ATGGTACACA GTGAGGGGAT TCTACTAATT 360
TACAAACAGA ACATTATTCC ATTTATGTTT AGAGTTAGGA AATATAGAAA AGTTGTTACA 420
ACAAGTACTG TCTACAATGG TATTTATTCT GACTCTATTA CCAACCAACA TACTTTCTAT 480
AAATCAATCG AACCTTGGGA GACAGAAAAG ATGGACACAA TATATCAGTG TTTTAATTCT 540
TTAAGACTAA ACACAGGTGG AAATCTGCTT ACTTATGTAG ATAGAGATGA TATAAATATG 600
ACAGTGTTTC TGCAACCTGT TGACGGTGTG ACGCCCGATG TGAAGAGGTA TGGCAGTCAA 660
CCAGAGCTGT ACCTTGAACC TGGCTGGTTT TGGGGTAGTT ATAGAAGACG AACTACAGTG 720
AACTGTGAAC TAATGGACAT GTTTGCAAGA TCAAATCCTC CATTTGATTT CTTTGTTACA 780
GCTACAGGTG ATACGGTGGA AATGTCTCCA TTTTGGAGTG GTGAAGATGA TCATGAAAAT 840
AAGATGCACG AGAAGCCATG GTTTGTTAGT GTGATAAATA ACTACAAGGT GGTGGACTAT 900
CAAAACAGAG GGACTGTACC CCTTGGAAAA ACAAGGATAT TTCTAGATAG GGAAGAGTAT 960
ACATTATCTT GGGAAAAGCA TCTAAAAAAT ATGTCATATT GTCCACTAAC ATTATGGAAA 1020
GCATTTTACA ATGGAATCCA GACGGAGCAT TCAGGCTCAT ATCATTTTGT AGCCAATGAC 1080
ATCACAGCGT CATTCACAAC TAGTAAAGAA GACATGAAAG AGTTCAATAC GACATATCAT 1140
TGTCTCAACG AGGAAATAAA GGCAGAAATA GAGAAGAAAT ATGCAAAAGT AAACTCAACT 1200
CACTCTAAAT ATGGAGATCT GAAATACTTT AAAACAGATG GGGGTCTCTA TTTAGTCTGG 1260
CAACCTCTTA TTCAAAACAG GCTTCTTGAT GCTAAGAACA AACTGAACAA TGAGACTTAT 1320
TCCAGGAGAT CACGACGTCA GGCAGAATCT ACTACTGACC CAATGATGGA GATGACTGGA 1380
AATGGAGCAG GTGGAGAATA TAGCAGTGAA AATTCAATCA CGGTGGCGCA GGTGCAGTAT 1440
GCCTATGACA ATCTTCGTAT CAGAATAAAT AACATTTTGG AAGATTTGTC AAAGGCATGG 1500
TGTCGTGAGC AGCATAGAGC TGCTCTGGTG TGGAATGAGC TCAGCAAGAT TAATCCCACA 1560
AGCGTCATGA GCATGATTTA CAATAGACCC GTATCAGCCA AAAGAATAGG AGATGTCATT 1620
TCAGTCTCTA ACTGTATTGT GGTAGACCAA ACCAGTGTCT CATTACATAA AAGTCTCAGG 1680
CTTCTCAGTG CATCGGATGA AAAGTGCTTC TCTAGACCTC CAGTGACATT TAAGTTTATG 1740
AATGACAGTA CTATTTACAA AGGGCAACTA GGAGTCAATA ATGAGATTCT CTTAACCACA 1800
ACATACCTTG AAACATGTCA GGAAAACACT GAGTATTACT TTCAGGCAAA GACAGACATG 1860
TACATTTACA AAAACTATGA GCATTTGAAG ACTGTGCCTT TATCTTCGAT CACCACACTA 1920
GATACATTTA TAGCCCTTAA TTTTACACTA TTGGAGAATG TTGACTTTAA AGTCATTGAA 1980
CTTTATACCA GGGACGAGAA GAGGCTTAGT AATGTCTTTG ACATTGAAAC AATGTTTAGG 2040
GAATATAACT ACTATGCTCA GAGGGTCAGT GGCCTCAGAA AGGATTTGCT GGATCTAAGC 2100
ACCAATAGAA ATCAATTTGT GGATGCATTT GGTAGTCTTA TGGATGATTT GGGTGCTGTT 2160
GGGCAGACAG TTGTAAATGC TGTAAGTGGT GTGGCTACGC TGTTTAGCTC AATTGTAACA 2220
GGATTTATTA ATTTCATTAA AAACCCATTT GGTGGAATGT TAATGATTAT TGTTGTTATT 2280
GGTGTGCTAT TTGCCATCTA CTTTCTGACC AAAAAGACGA AGATATATGA GACGGCACCG 2340
ATTAAGATGA TTTATCCTGA AATTGACAAG CTGAAAGAAC GTGAGGGAAA ATCAGAAATA 2400
GCACCAATCA GTGAAGAAGA GCTGGAGAGA ATTGTACTTG CTATGCACAT CCATCAACAA 2460
AATTCACATA TGGAAACAAA AACAAGGAAG GATCCCAAAG ACAGCATATT AACAAGGGCA 2520
CAAAATATGC TACGCAAAAG ATCAGGATAT TCTAATTTAA AAAATGCTGA ATCTGTGGAG 2580
ATGTTAAACA CTTTATAA                                              2598
```

Figure 3

```
MAGSLKLRGS VLALWYLYQV ALYSLSIAET GVTSPPNTAT WSTESPLTGH    50
YGTHDSSHGE RGNNENRDSE EQNKNIYGSP STFPYRVCSA SGVGDVFRFQ   100
TDHVCPDASD MVHSEGILLI YKQNIIPFMF RVRKYRKVVT TSTVYNGIYS   150
DSITNQHTFY KSIEPWETEK MDTIYQCFNS LRLNTGGNLL TYVDRDDINM   200
TVFLQPVDGV TPDVKRYGSQ PELYLEPGWF WGSYRRRTTV NCELMDMFAR   250
SNPPFDFFVT ATGDTVEMSP FWSGEDDHEN KMHEKPWFVS VINNYKVVDY   300
QNRGTVPLGK TRIFLDREEY TLSWEKHLKN MSYCPLTLWK AFYNGIQTEH   350
SGSYHFVAND ITASFTTSKE DMKEFNTTYH CLNEEIKAEI EKKYAKVNST   400
HSKYGDLKYF KTDGGLYLVW QPLIQNRLLD AKNKLNNETY SRRSRRQAES   450
TTDPMMEMTG NGAGGEYSSE NSITVAQVQY AYDNLRIRIN NILEDLSKAW   500
CREQHRAALV WNELSKINPT SVMSMIYNRP VSAKRIGDVI SVSNCIVVDQ   550
TSVSLHKSLR LLSASDEKCF SRPPVTFKFM NDSTIYKGQL GVNNEILLTT   600
TYLETCQENT EYYFQAKTDM YIYKNYEHLK TVPLSSITTL DTFIALNFTL   650
LENVDFKVIE LYTRDEKRLS NVFDIETMFR EYNYYAQRVS GLRKDLLDLS   700
TNRNQFVDAF GSLMDDLGAV GQTVVNAVSG VATLFSSIVT GFINFIKNPF   750
GGMLMIIVVI GVLFAIYFLT KKTKIYETAP IKMIYPEIDK LKEREGKSEI   800
APISEEELER IVLAMHIHQQ NSHMETKTRK DPKDSILTRA QNMLRKRSGY   850
SNLKNAESVE MLNTL                                         865
```

Figure 4

```
pGHV-gpB DNA.txt        ---------- ---------- -----AATCT TCGTATCAGA ATAAATAACA      25
pGHV1 DNA.641-1300)     CGCCGCCGTC CGGCTCCACG GTGGTGCGGC TGGAGCCCGA GCAGGC--CT      688
                                                         T G   C GA   A     C

pGHV-gpB DNA.txt        TTTTGGAAGA TTTGTCAAAG GCATGGTGTC GTGAGCAGCA TAGAGCTGCT      75
pGHV1 DNA.(641-1300)    GCCCCGAGTA CTCG-CAGGG GCGCAACTTC ACGGAGGGGA TCGCCGTGCT      737
                             GA  A  T G CA  G GC      TC   G    G A T G   TGCT

pGHV-gpB DNA.txt        CTGGTGTGGA ATGAGCTCAG CAAGATTAAT CCCACAAGCG TCATGAGCAT      125
pGHV1 DNA.(641-1300)    CT----T-CA AGGAGAACAT C--G-CC--C CGCACAAGT- TCAAGGCCCA      776
                        CT    T  A A GAG  CA  C  G       C CACAAG   TCA G  C

pGHV-gpB DNA.txt        GATTTACAAT -AGACCCGTA TCAGC-CAAA AGAATAG-GA GATGTCATTT      172
pGHV1 DNA.(641-1300)    CATCTACTAC AAGAACGTCA TCGTCACGAC CGTGTGGTCC GGGAGCACGT      826
                         AT TAC A   AGA C   A TC  C C A   G  T G    G    CA  T

pGHV-gpB DNA.txt        CAGTCTCTAA C-TGTATTG- -TGGTAGACC AAACCAGTGT CTCATTACAT      219
pGHV1 DNA.(641-1300)    ACGCGGCCAT CACGAACCGC TTCACAGACC GCGTGCCCGT CCCCGTGCAG      876
                          G   C A  C  G A  G   T   AGACC         GT C C  T CA

pGHV-gpB DNA.txt        AAAAGTCTCA GGCTTCTCAG TGCATCGGAT GAAAAGTGCT TCTCTAGACC      269
pGHV1 DNA.(641-1300)    GAGA-TCACG GACGTGATCG ACCGCCG--C GGCAAGTGCG TCTCCA-AGG      922
                         A A TC C    C T    G   C  CG    G  AAGTGC  TCTC A A

pGHV-gpB DNA.txt        TCCAGTGACA T--TTAA-GT TTATGA-ATG ACAGTACT-A TTTACAAAGG      314
pGHV1 DNA.(641-1300)    CCGAGT-ACG TGCGCAACAA CCACAAGGTG ACCGCCTTCG ACCGCGACGA      971
                         C AGT AC  T    AA      A  A  TG AC G   T       C AG

pGHV-gpB DNA.txt        GCAACTAG-- GAGTCAATAA TGAGATTCT- ----CTTAAC ---CACAACA      354
pGHV1 DNA.(641-1300)    GAACCCCGTC GAGGTGGACC TGCGCCCCTC GCGCCTGAAC GCGCTCGGCA      1021
                        G A C      GAG        TG G   CT      CT AAC    C    C

pGHV-gpB DNA.txt        TAC-C--TTG AAACA-TGTC -AGGAAA--- ACACTGAGTA TTAC-TTTCA      395
pGHV1 DNA.(641-1300)    CCCGCGGCTG GCACACCACC AACGACACCT ACACCAAGAT CGGCGCCGCG      1071
                          C C   TG   ACA     C  A GA A    ACAC  AG      C    C

pGHV-gpB DNA.txt        GGCAAAGACA GACATGTACA TTTACAAAAA CT--AT---- GAGCATTTGA      439
pGHV1 DNA.(641-1300)    GGCTTCTAC- CACACGGGCA CCTCCGTCAA CTGCATCGTC GAGGAGGTGG      1120
                        GGC    AC   ACA G  CA   T C   AA CT  AT     GAG A  TG

pGHV-gpB DNA.txt        AGAC------ --TGTGCCTT TA-----TCT TCGATCACCA CACTAGATAC      476
pGHV1 DNA.(641-1300)    AGGCGCGCTC CGTGTACCCC TACGACTCCT TCGCCCTGTC CACGGGGGAC      1170
                        AG C         TGT CC   TA       CT TCG  C     CAC  G  AC

pGHV-gpB DNA.txt        ATT---TATA GCCCTTAATT TTAC--ACTA TTGGAGAATG TTGACTTTAA      521
pGHV1 DNA.(641-1300)    ATTGTGTACA TGTCCCCCTT CTACGGCCTG CGCGAGGGGG CCCACGGGGA      1220
                        ATT   TA A    C    TT  TAC    T     GAG   G    AC    A

pGHV-gpB DNA.txt        AGTCATTGAA CTTTATACCA GGG----ACG AG-AAGAGGC TTAGTA--AT      564
pGHV1 DNA.(641-1300)    GCACATCG-G CTACGCGCCC GGGCGCTTCC AGCAGGTGGA GCACTACTAC      1269
                           CAT G   CT     CC  GGG     C  AG    G GG    A TA  A

pGHV-gpB DNA.txt        GTCTTTGACA TTGAAACAAT G--------- --   585
pGHV1 DNA.(641-1300)    CCCATCGAC- CTGGACTCGC GCCTCCGCGC CT   1300
                          C T GAC   TG A      G
```

Figure 5

```
pGHV-gpB prot          ---------- ---------- ---------N LRI------- ----------   4
PGHV1Prot.(491-850)    PAAPAAARRA RRSPGPAGTP EPPAVNGTGH LRITTGSAEF ARLQFTYDHI   540
                                                        LRI

pGHV-gpB prot          --RINNILED LSKAWCREQH RAALVWNELS KINPTSVMSM IYNRPVSAKR   52
PGHV1Prot.(491-850)    QAHVNDMLGR IAAAWCELQN KDRTLWSEMS RLNPSAVATA ALGQRVSARM   590
                           N  L       AWC   Q        W E S   NP  V          VSA

pGHV-gpB prot          IGDVISVSNC IVVDQTSVSL HKSLRLLSAS DEKCFSRPPV TFKFMNDSTI   102
PGHV1Prot.(491-850)    LGDVMAISRC VEV-RGGVYV QNSMR-VPGE RGTCYSRPLV TFE-HNGTGV   637
                        GDV   S C   V    V     S R          C SRP V TF   N

pGHV-gpB prot          YKGQLGVNNE ILLTTTYLET CQENTEYYFQ AKTDMYIYKN YEHLKTVPLS   152
PGHV1Prot.(491-850)    IEGQLGDDNE LLISRDLIEP CTGNHRRYFK LGSGYVYYED YNYVRMVEVP   687
                         GQLG  NE  L      E  C  N   YF          Y   Y     V

pGHV-gpB prot          SITTLDTFIA LNFTLLENVD FKVIELYTRD E--------- ----KR----   185
PGHV1Prot.(491-850)    --ETISTRVT LNLTLLEDRE FLPLEVYTRE ELADTGLLDY SEIQRRNQLH   735
                             T    LN TLLE     F   E YTR  E               R

pGHV-gpB prot          -------- ---------- ---------- ---------- ----------   185
PGHV1Prot.(491-850)    ALKFYDIDRV VKVDHNVVLL RGIANFFQGL GDVGAAVGKV VLGATGAVIS   785


pGHV-gpB prot          --------LS NVF------- ---------- ---------- ----------   190
PGHV1Prot.(491-850)    AVGGMVSFLS NPFGALAIGL LVLAGLVAAF LAYRHISRLR RNPMKALYPV   835
                               LS N F

pGHV-gpB prot          --------DI E--TM        195
PGHV1Prot.(491-850)    TTKTLKEDGV DEGDV        850
```

Figure 6

```
pGHV-gpB DNA.txt      ---------- ---------- ---------- ---------- ----------
pGHV2 DNA.txt         CCAGCATAAT GATAGCCAAT AATCTGTGTT ACTCTACCCT GATCTTAAAT    50

pGHV-gpB DNA.txt      ---------- ---------- ---------- ---------- -----AATCT    5
pGHV2 DNA.txt         GACGAGGACG TGACGGGGAT CGACGAGAAA GATATTCTGA CGGTGCATGT    100
                                                                       AT T

pGHV-gpB DNA.txt      TCGTATCAGA ATA-AAT-AA CATTTTGGAA GATTTGTCAA AGGCATGGTG    53
pGHV2 DNA.txt         --AAACAAGA ATACCGTGTA CAGGTTCG-T TAGGAG-CAG CGTCAGGGAG    146
                          A  AGA ATA   T  A CA  TT G    A   G CA   G CA GG G

pGHV-gpB DNA.txt      TC-GTGAGCA GCATAGAGCT GCTCTGGTGT GGAATGAGCT CAGCAAGATT    102
pGHV2 DNA.txt         TCTATACTCG GCAC---GCT GCT---GTCT AG-ATG-GCT CAGGAAGAGA    188
                      TC  T   C  GCA    GCT GCT   GT T  G ATG GCT CAG AAGA

pGHV-gpB DNA.txt      AATCCCACAA GCG-TCATGA GCATGATTTA CAAT-AGACC CGTAT-CAGC    149
pGHV2 DNA.txt         AA----GGAA GTGAAGGCGC GCATGAAACG CTGTGAGGAC CCTATGTTGG    234
                      AA      AA G G     G  GCATGA     C  T AG  C C TAT   T

pGHV-gpB DNA.txt      CAAAAGAATA GGAGATGTCA TTTCAGTCTC TAACTGTATT GTGGTAGACC    199
pGHV2 DNA.txt         C-ACTG-AT- --ACTTGACA -AGCAGCAGC TTGC--CCTC AAGGT-GAC-    274
                      C A  G AT    A  TG CA    CAG   C T  C    T    GGT GAC

pGHV-gpB DNA.txt      AAACCAGTGT CTCATTACAT AAAAGTCTCA GGCTTCTCAG TGCATCGGAT    249
pGHV2 DNA.txt         -GTGCAATGC GTT-TTAC-- ---GGCTTCA CGGGAGCC-G TGCA-CGG-T    314
                          CA TG   T  TTAC       G  TCA  G     C G TGCA CGG T

pGHV-gpB DNA.txt      GAAAAGTGCT TCTCTAGACC TCCAGTGACA TTTAAGTTTA TGAATGACAG    299
pGHV2 DNA.txt         CTGCTGC-CG TGTCT--CCC TCTAGCGGCG TCCA---TCA CCAGC-ATAG    357
                           G  C  T TCT   CC TC AG G C  T  A   T A   A   A AG

pGHV-gpB DNA.txt      TACTATTTAC AAAGGGCAAC TAGGAGTCAA TAATGAGATT CTCTTAACCA    349
pGHV2 DNA.txt         GGC--GGGAC A---TGC--T TAGG---CA- -GACGAG-TG ACTTTATCAA    394
                        C     AC A    GC    TAGG   CA    A GAG T     TTA C A

pGHV-gpB DNA.txt      CAACATACCT TGAAACATGT CAGGAAAACA CTGAGTATTA CTTTCAGGCA    399
pGHV2 DNA.txt         CAATGT-CCT T-----TCGT CTAGAGAATA CG-------- ----------    420
                      CAA  T CCT T       GT C  GA AA A C

pGHV-gpB DNA.txt      AAGACAGACA TGTACATTTA CAAAAACTAT GAGCATTTGA AGACTGTGCC    449
pGHV2 DNA.txt         ---------- ---------- ---------- ---------- ----------    420

pGHV-gpB DNA.txt      TTTATCTTCG ATCACCACAC TAGATACATT TATAGCCCTT AATTTTACAC    499
pGHV2 DNA.txt         ---------- ---------- ---------- ---------- ----------    420

pGHV-gpB DNA.txt      TATTGGAGAA TGTTGACTTT AAAGTCATTG AACTTTATAC CAGGGACGAG    549
pGHV2 DNA.txt         ---------- ---------- ---------- ---------- ----------    420

pGHV-gpB DNA.txt      AAGAGGCTTA GTAATGTCTT TGACATTGAA ACAATG         585
pGHV2 DNA.txt         ---------- ---------- ---------- ------         420
```

Figure 7

```
pGHV-gpB prot     NLRIRINNIL EDLSKAWCRE QHRAALVWNE LSKINPTSVM SMIYNRPVSA    50
pGHV2 prot.txt    S--IMIANNL -------C-- --YSTLI--- LNDEDVTG-- -------IDE    25
                     I I N L        C          L      L     T

pGHV-gpB prot     KRIGDVISVS NCIVVDQTSV SLHKSLRLLS ASDEKCFSRP PVTFKFMNDS   100
pGHV2 prot.txt    K---DILTVH ----VNKNTV ---------- ---------- ---YRFVRSS    45
                  K   D   V      V    V                            F   S

pGHV-gpB prot     ---TIYKGQL GV-NNEILLT TTYLETCQEN TEYYFQAKTD MYI---YKN-   142
pGHV2 prot.txt    VRESILGTLL SRWLRKRKEV KARMKRCEDP MLALILDKQQ LALKVTCNAF    95
                      I    L                   C          K

pGHV-gpB prot     YEHLKTVP-- LSSITTLDTF IALNFTLL-E NVDFKVIELY TRD---EK-R   185
pGHV2 prot.txt    YGFTGAVHGL LPCLPLAASI TSIGRDMLRQ TSDFINNVLS SREYVSEKFS   145
                  Y     V    L                 L     DF    L   R    EK

pGHV-gpB prot     LSNV-F--DI ETM-    195
pGHV2 prot.txt    LSDGDFQGDF SPEC    159
                  LS   F  D
```

Figure 8

```
pGHV-gpB DNA      AATCTTCGTA TCAGAATAAA TAACATTTTG GAAGATTTGT CAAAGGCATG    50
AF118399 DNA.txt  ---------- ---------- ---------- ---------- ----------

pGHV-gpB DNA      GTGTCGTGAG CAGCATAGAG CTGCTCTGGT GTGGAATGAG CTCAGCAAGA    100
AF118399 DNA.txt  ---------- ---------- ---------- ---------- ----------

pGHV-gpB DNA      TTAATCCCAC AAGCGTCATG AGCATGATTT ACAATAGACC CGTATCAGCC    150
AF118399 DNA.txt  ---------- ---------- ---------- ---------- ----------

pGHV-gpB DNA      AAAAGAATAG GAGATGTCAT TTCAGTCTCT AACTGTATTG TGGTAGACCA    200
AF118399 DNA.txt  ---------- ---------- ---------- ---------- ----------

pGHV-gpB DNA      AACCAGTGTC TCATTACATA AAAGTCTCAG GCTTCTCAGT GCATCGGATG    250
AF118399 DNA.txt  ---------- ---------- ---------- ---------- ----------

pGHV-gpB DNA      AAAAGTGCTT CTCTAGACCT CCAGTGACAT TTAAGTTTAT GAATGACAGT    300
AF118399 DNA.txt  ---------- ---------- ---------- ------TAAT CTATGTCACT    14
                                                     T AT   ATG CA T

pGHV-gpB DNA      ACTATTTACA AAGGGCAACT AGGA-GTCAA TAATGAGATT CTCTTAACCA    349
AF118399 DNA.txt  -CTACCC-TA ATCCATCATG AAGACCTGCA TAAATATCCT CAATTAAAGG    62
                   CTA     A A      A  A GA  T  A TAA  A   T A  TTAA

pGHV-gpB DNA      CAACATACCT TGAAACATGT CAGGAAAACA CTGAGTATTA CTTTCAGGCA    399
AF118399 DNA.txt  AGGAGGATTA TGAAACAT-- ---------- ---------- -TTT------    83
                        A    TGAAACAT                          TTT

pGHV-gpB DNA      AAGACAGACA TGTACATTTA CAAAAACTAT GAGCATTTGA AGACTGTGCC    449
AF118399 DNA.txt  ---------- TG---ATT-- ---------- -AG---TT-- ---CTG----    95
                             TG   ATT               AG   TT      CTG

pGHV-gpB DNA      TTTATCTTCG ATCACCACAC TAGATACATT TATAGCCCTT AATTTTACAC    499
AF118399 DNA.txt  ---------- ---------- ---------- ----GTCC-- ----------    99
                                                      GTCC

pGHV-gpB DNA      TATTGGAGAA TGTTGACTTT ------AAAG TCAT-T--GA A---CTT---    534
AF118399 DNA.txt  ---------- TGTTCACTTT GTAAAAAAAC ACATATCAGA ATCTCTTCTG    139
                             TGTT ACTTT       AAA   CAT T  GA A   CTT

pGHV-gpB DNA      --TA------ -TAC--CA-- G--GG--ACG AGA------- --AG--AGG-    555
AF118399 DNA.txt  TCTAACCTGC TTACAACATG GCTGGCTAAG AGAAAAATGA TCAGAAAGGA    189
                    TA        TAC  CA   G  GG  A G AGA          AG  AGG

pGHV-gpB DNA      CTTAGTA--A TGT-CT--TT GACA-TTGA- AACAATG--- ----------    585
AF118399 DNA.txt  ATTAGCAGCA TGTGCTGACC CAAAGCTCAG GACAAT-TTT AGATAAACAG    238
                   TTAG A  A TGT CT      A A  T A  ACAAT

pGHV-gpB DNA      ---------- ---------- ---------- ---------- ----------    585
AF118399 DNA.txt  CAGCTTGCAA TTAAGGTGAC ATGCAATGCT GTGTATGGGT TCACTGGTGT    288

pGHV-gpB DNA      ---------- ---------- ---------- ---------- ----------    585
AF118399 DNA.txt  TGCATCTGGT ATGCTGCCCT GTCTCAAGAT TGCAGAGACC ATAACTATGC    338

pGHV-gpB DNA      ---------- ---------- ---------- ---------- ----------    585
AF118399 DNA.txt  AAGGAAGGGC CATGTTGGAA AAGACAAAAG TATTTGTAGA GAATTTAAGT    388

pGHV-gpB DNA      ---------- ---------- ---------- ---------- ----------    585
AF118399 DNA.txt  CATGAGGATC TCCATTCCAT CTGTAAGGTT GGCTTTATGC CTCAGTCACC    438

pGHV-gpB DNA      ---------- ---------- --------        585
AF118399 DNA.txt  AAACAGCATT GATAAACCCT TCAAGGTG        466
```

Figure 9

```
pGHV-gpB DNA      ---------- ---------- ---------- ---------- ----------
AF118401 DNA.txt  GAGGACCTGC ATAAGTATCC TCAATTAAAG GAGGATGATT ATGAAACATT   50

pGHV-gpB DNA      ---------- ---------- ---------- ---AATCTTC GTATCAGAAT   17
AF118401 DNA.txt  TTTGATTAGT TCTGGCCCTG TTCACTTTGT AAAAAAACAC ATATCAGAAT  100
                                                      AA      C   TATCAGAAT

pGHV-gpB DNA      AAATAACATT TTGGAAGATT TGTCAAAGGC ATGGTGTCGT GAGCAGCATA   67
AF118401 DNA.txt  ------C-TC TT-------- ---------- ---------- ----------  105
                        C T   TT

pGHV-gpB DNA      GAGCTGCTCT GGTGTGGAAT GAGCTCAGCA AGATTAATCC CACAAGCGTC  117
AF118401 DNA.txt  ---CTG-TC- ------GAA- ---CTT---- -G------CT CACAA----C  125
                     CTG TC         GAA     CT      G      C  CACAA    C

pGHV-gpB DNA      ATGAGCATGA TTTACAATAG ACCCGTATCA GCCAAAAGAA ------T---  158
AF118401 DNA.txt  ATG-GC-TG- ---------- ---------- GCCAAGAGAA AAATGATCAG  152
                  ATG GC TG                                          T

pGHV-gpB DNA      --AGG----- --AG-ATGT- ---------- --------CA --TTT-----  172
AF118401 DNA.txt  AAAGGAATTG ACAGCATGTG CTGATCCAAA GCTCAGGACA ATTTTAGATA  202
                    AGG         AG ATGT                         CA    TTT

pGHV-gpB DNA      -----CAGTC T----CTA-- ---AC-TGTA TTG-TG-GTA --GA-CCA--  200
AF118401 DNA.txt  AACAGCAGCT TGCAATTAAG GTGACATGCA ATGCTGTGTA TGGATTCACT  252
                       CAG    T    TA       AC TG A  TG TG GTA    GA CA

pGHV-gpB DNA      --------A- -----AC-CA G---TGTCTC A--------- ------TTAC  217
AF118401 DNA.txt  GGTGTTGCAT CTGGTATGCT GCCATGTCTC AAGATTGCAG AGACCATCAC  302
                          A        A  C  G   TGTCTC A                TCAC

pGHV-gpB DNA      ---------- ---------- --------AT AAAAGT--CT -CAG-GCTTC  235
AF118401 DNA.txt  TATGCAAGGA AGGGCCATGT TGGAAAAGAC AAAAGTATTT GTAGAGAATC  352
                                                 A   AAAAGT  T    AG G TC

pGHV-gpB DNA      TCAG---TGC A----TCGGA T-GAAAAGT- -GCTT--CTC TAGACCTCCA  273
AF118401 DNA.txt  TGAGTCATGA AGATCTCCGT TCCATATGTA AGGTTGGCTC TATACCTC-A  401
                  T AG   TG  A    TC G  T  A A GT   G TT  CTC TA ACCTC A

pGHV-gpB DNA      GTGACATTTA AGTTTATGAA TGACAGTACT ATTTACAAAG GCAACTAGG   323
AF118401 DNA.txt  GT--CA-TCA A----ACG-- TG-------- -TTT------ ----------  417
                  GT  CA T A A    A G   TG          TTT

pGHV-gpB DNA      AGTCAATAAT GAGATTCTCT TAACCACAAC ATACCTTGAA ACATGTCAGG  373
AF118401 DNA.txt  -G---ATAAA ---------- ---------- ---------- ----------  423
                   G    ATAA

pGHV-gpB DNA      AAAACACTGA GTATTACTTT CAGGCAAAGA CAGACATGTA CATTTACAAA  423
AF118401 DNA.txt  ---------- ---------- ---------- ---------- ----------  423

pGHV-gpB DNA      AACTATGAGC ATTTGAAGAC TGTGCCTTTA TCTTCGATCA CCACACTAGA  473
AF118401 DNA.txt  ---------- ---------- ---------- ---------- ----------  423

pGHV-gpB DNA      TACATTTATA GCCCTTAATT TTACACTATT GGAGAATGTT GACTTTAAAG  523
AF118401 DNA.txt  ---------- ---------- ---------- ---------- ----------  423

pGHV-gpB DNA      TCATTGAACT TTATACCAGG GACGAGAAGA GGCTTAGTAA TGTCTTTGAC  573
AF118401 DNA.txt  ---------- ---------- ---------- ---------- ----------  423

pGHV-gpB DNA      ATTGAAACAA TG   585
AF118401 DNA.txt  ---------- --   423
```

Figure 10

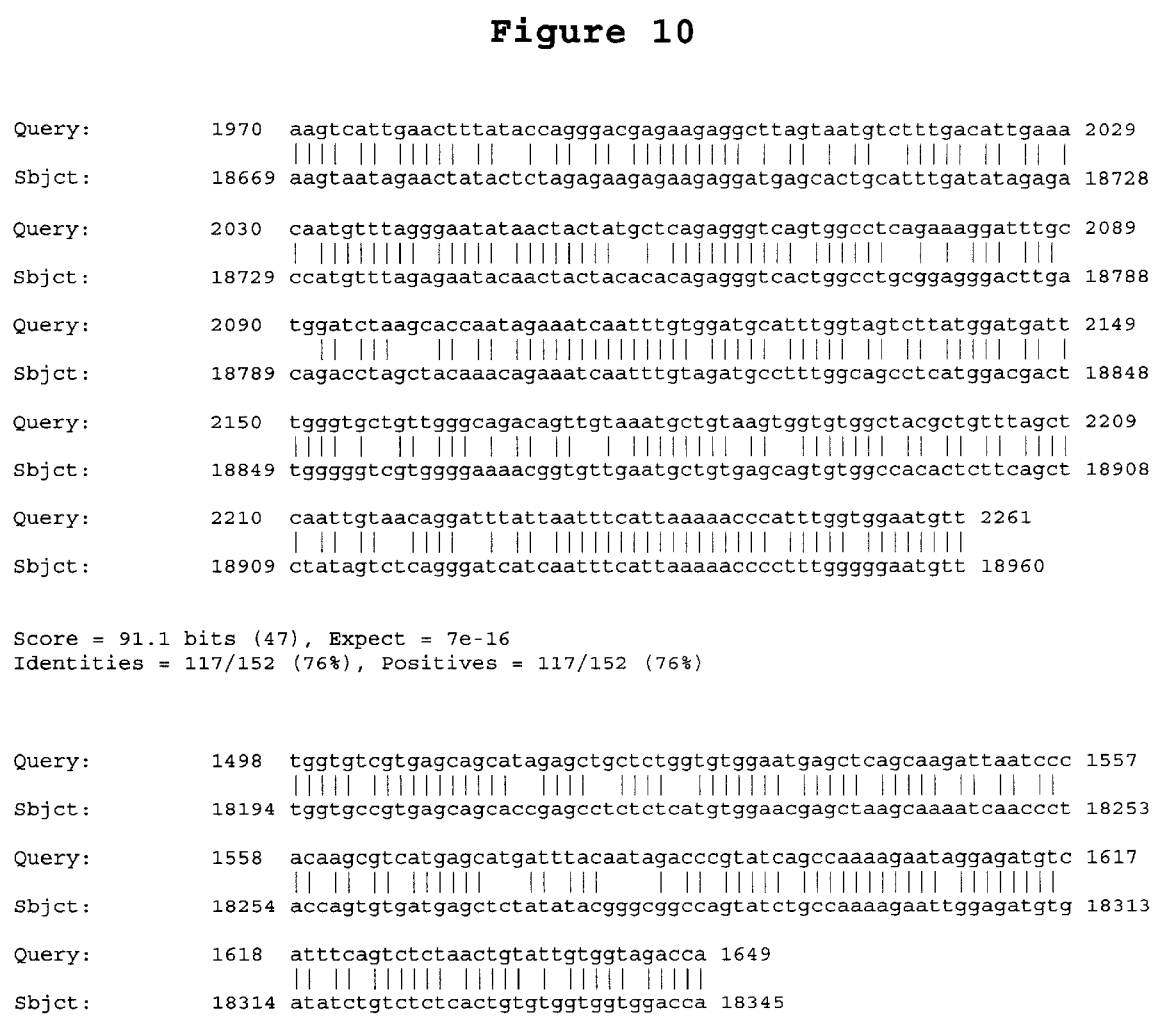

```
Query:  1970  aagtcattgaactttataccagggacgagaagaggcttagtaatgtctttgacattgaaa 2029
Sbjct:  18669 aagtaatagaactatactctagagaagagaagaggatgagcactgcatttgatatagaga 18728

Query:  2030  caatgtttagggaatataactactatgctcagagggtcagtggcctcagaaaggatttgc 2089
Sbjct:  18729 ccatgtttagagaatacaactactacacacagagggtcactggcctgcggagggacttga 18788

Query:  2090  tggatctaagcaccaatagaaatcaatttgtggatgcatttggtagtcttatggatgatt 2149
Sbjct:  18789 cagacctagctacaaacagaaatcaatttgtagatgcctttggcagcctcatggacgact 18848

Query:  2150  tgggtgctgttgggcagacagttgtaaatgctgtaagtggtgtggctacgctgtttagct 2209
Sbjct:  18849 tgggggtcgtggggaaaacggtgttgaatgctgtgagcagtgtggccacactcttcagct 18908

Query:  2210  caattgtaacaggatttattaatttcattaaaaacccatttggtggaatgtt 2261
Sbjct:  18909 ctatagtctcagggatcatcaatttcattaaaaacccctttgggggaatgtt 18960
```

Score = 91.1 bits (47), Expect = 7e-16
Identities = 117/152 (76%), Positives = 117/152 (76%)

```
Query:  1498  tggtgtcgtgagcagcatagagctgctctggtgtggaatgagctcagcaagattaatccc 1557
Sbjct:  18194 tggtgccgtgagcagcaccgagcctctctcatgtggaacgagctaagcaaaatcaaccct 18253

Query:  1558  acaagcgtcatgagcatgatttacaatagacccgtatcagccaaaagaataggagatgtc 1617
Sbjct:  18254 accagtgtgatgagctctatatacgggcggccagtatctgccaaaagaattggagatgtg 18313

Query:  1618  atttcagtctctaactgtattgtggtagacca 1649
Sbjct:  18314 atatctgtctctcactgtgtggtggtggacca 18345
```

Figure 11(a)

```
gi|2337975 (AF005370) glycoprotein B [Alcelaphine herpesvirus 1]
          Length = 854

 Score =  953 bits (2437), Expect = 0.0
 Identities = 463/804 (57%), Positives = 589/804 (72%), Gaps = 26/804 (3%)

Query: 74  KNIYGSPSTFPYRVCSASGVGDVFRFQTDHVCPDASDMVHSEGILLIYKQNIIPFMFRVR 133
            K I+  PS FP+RVCSAS +GD+FRFQT H CP+  D  H+EGILLI+K+NI+P++F+VR
Sbjct: 55  KGIHSDPSAFPFRVCSASNIGDIFRFQTSHSCPNTKDKEHNEGILLIFKENIVPYVFKVR 114

Query: 134 KYRKVVTTSTVYNGIYSDSITNQHTFYKSIEPWETEKMDTIYQCFNSLRLNTGGNLLTYV 193
            KYRK+VTTST+YNGIY+D++TNQH F KS+  +ET +MDTIYQC+NSL +  GGNLL Y
Sbjct: 115 KYRKIVTTSTIYNGIYADAVTNQHVFSKSVPIYETRRMDTIYQCYNSLDVTVGGNLLVYT 174

Query: 194 DRDDINMTVFLQPVDGVTPDVKRYGSQPELYLEPGWFWGSYRRRTTVNCELMDMFARSNP 253
            D D  NMTV LQPVDG++  V+RY SQPE++ EPGW  G YRRRTTVNCE+ +  AR+ P
Sbjct: 175 DNDGSNMTVDLQPVDGLSNSVRRYHSQPEIHAEPGWLLGGYRRRTTVNCEVTETDARAVP 234

Query: 254 PFDFFVTATGDTVEMSPFWSGEDDHENKMHEKPWFVSVINNYKVVDYQNRGTVPLGKTRI 313
            PF +F+T  GDT+EMSPFWS    +     E    ++V  +Y+VVDY+ RGT P G TRI
Sbjct: 235 PFRYFITNIGDTIEMSPFWSKAWNETEFSGEPDRTLTVAKDYRVVDYKFRGTQPQGHTRI 294

Query: 314 FLDREEYTLSWEKHLKNMSYCPLTLWKAFYNGIQTEHSGSYHFVANDITASFTTSKEDMK 373
            F+D+EEYTLSW +  +N+SYC    WK+F N I+TEH  S HFVANDITASF T     +
Sbjct: 295 FVDKEEYTLSWAQQFRNISYCRWAHWKSFDNAIKTEHGKSLHFVANDITASFYTPNTQTR 354

Query: 374 EFNTTYHCLNXXXXXXXXXXXXXVNSTHSKYGDLKYFKTDGGLYLVWQPLIQNRLLDAKN 433
            E    + CLN             VN THS  G  +Y+ T+GGL LVWQPL+Q +LLDAK
Sbjct: 355 EVLGKHVCLNNTIESELKSRLAKVNDTHSPNGTAQYYLTNGGLLLVWQPLVQQKLLDAKG 414

Query: 434 KLN---------NETYSRRSRRQAESTTDPMMEMTGNGAGGEYSSENSITVAQVQYAYDN 484
             L+           T + RSRRQ  S +        +G    Y++E++I + Q+Q+AYD
Sbjct: 415 LLDAVKKQQNTTTTTTTTRSRRQRRSVS--------SGIDDVYTAESTILLTQIQFAYDT 466

Query: 485 LRIRINNILEDLSKAWCREQHRAALVWNELSKINPTSVMSMIYNRPVSAKRIGDVISVSN 544
            LR +INN+LE+LS+AWCREQHRA+L+WNELSKINPTSVMS IY RPVSAKRIGDVISVS+
Sbjct: 467 LRAQINNVLEELSRAWCREQHRASLMWNELSKINPTSVMSSIYGRPVSAKRIGDVISVSH 526

Query: 545 CIVVDQTSVSLHKSLRLLSA-SDEKCFSRPPVTFKFMNDSTIYKGQLGVNNEILLTTTYL 603
            C+VVDQ SVSLH+S+R+       +C+SRPPVTFKF+NDS +YKGQLGVNNEILLTTT +
Sbjct: 527 CVVVDQDSVSLHRSMRVPGRDKTHECYSRPPVTFKFINDSHLYKGQLGVNNEILLTTTAV 586

Query: 604 ETCQENTEYYFQAKTDMYIYKNYEHLKTVPLSSITTLDTFIALNFTLLENVDFKVIELYT 663
            E C ENTE+YFQ   +MY YKNY H+KT+P+  + TLDTF+ LN TL+EN+DF+VIELY+
Sbjct: 587 EICHENTEHYFQGGNNMYFYKNYRHVKTMPVGDVATLDTFMVLNLTLVENIDFQVIELYS 646

Query: 664 RDEKRLSNVFDIETMFREYNYYAQRVSGLRKDLLDLSTNRNQFVDAFGSLMDDLGAVGQT 723
            R+EKR+S  FDIETMFREYNYY QRV+GLR+DL DL+TNRNQFVDAFGSLMDDLG VG+T
Sbjct: 647 REEKRMSTAFDIETMFREYNYYTQRVTGLRRDLTDLATNRNQFVDAFGSLMDDLGVVGKT 706
```

Figure 11(b)

```
Query: 724 VVNAVSGVATLFSSIVTGFINFIKNPFGGMLMIIVVIGVLFAIYFLTKKTKIYETAPIKM 783
           V+NAVS VATLFSSIV+G INFIKNPFGGML+  ++  V+  +  L +K K +   P++M
Sbjct: 707 VLNAVSSVATLFSSIVSGIINFIKNPFGGMLLFGLIAAVVITVILLNRKAKRFAQNPVQM 766

Query: 784 IYPEIDKLKEREGKSEIAPISEEELERIVLAMHIHQQNSHMETK-------TRKDPKDSI 836
           IYP+I  +  +  + ++ PIS+ EL+RI+LAMH +  +   E+K       T   P D
Sbjct: 767 IYPDIKTITSQREELQVDPISKHELDRIMLAMHDYHASKQPESKQDEEQGSTTSGPAD-W 825

Query: 837 LTRAQNMLRKRSGYSNLKNAESVE 860
           L +A+N+LR+R+GY  LK  +S E
Sbjct: 826 LNKAKNVLRRRAGYKPLKRTDSFE 849
```

GAMMA-HERPES VIRUS DNA AND METHODS OF USE

This application claims the benefit of U.S. Provisional Application No. 60/168,532, filed Dec. 2, 1999, and U.S. Provisional Application No. 60/142,736, filed Jul. 8, 1999, the disclosures of which are hereby incorporated by reference in their entirety.

FIELD OF THE INVENTION

The present invention relates to newly identified polynucleotides, polypeptides, and fragments thereof encoded by porcine gamma-herpesvirus sequences, and methods of using the porcine gamma-herpesvirus nucleic acids and polypeptides.

BACKGROUND OF THE INVENTION

Organ procurement currently poses one of the major problems in solid organ transplantation, since the number of patients requiring transplants far exceeds the number of organs available. One means of eliminating the shortage of donor organs for allotransplantation is to develop the technologies required to transplant non-human organs into humans, i.e., xenotransplantation. The development of clinical xenotransplantation will also allow for the transplantation of non-human cells and tissues.

A potential problem lies in the fact that human and animal organs may be of very different size, depending on the species serving as donor, and on the possibility of infection due to microorganisms present in the donor tissues and having an ability to infect humans. Consequently, one strain of the domesticated pig, denoted miniature swine (*Sus scrofa*), appears suitable for such transplants because of its similar size to humans (see below). Furthermore, any use of pigs as organ donors in xenotransplantation would obviate problems associated with the consideration of non-human primates as donors. Xenografts from non-human primates, for example, present considerable risk of transmission of pathogens and the consequent development of emerging infections. In addition, several pathogens that cause disease are known to infect both humans and non-human primates, for example, in the transmission of HIV from the chimpanzee to humans. Furthermore, chimpanzees and orangutans, the closest non-human primates phylogenetically, are endangered species and far too rare to be considered for organ transplantation purposes. Baboons are too small to be an appropriate donor for most organ transplants. Even the largest baboons weigh less than 40 kg. In addition, the gestation times and productivity of primates would not allow a commercially significant generation of source animals.

The physiology of many organ systems of pigs has been shown to be highly similar to the human counterparts (Sachs, D. H. (1994) *Veterinary Immunology & Immunopathology* 43:185–191). Thus, the miniature swine offers numerous advantages as potential xenograft donors. They achieve adult weights of approximately 100–150 kg, a size that is more compatible to human weights than that of the domestic pig, which reaches weights of over 500 kg. Through a selective breeding program over the past 20 years, partially inbred, miniature swine have been produced (Sachs et al. (1976) *Transplantation* 22: 559–567; Sachs, D. H. (1992) In *Swine as models in biomedical research*, eds M. Swindle, D. Moody, and L. Phillips, pp. 3–15. Ames Iowa State Univ. Press; Sachs, (1994) *Veterinary Immunology & Immunopathology* 43: 185–191). This breeding program has resulted in herds of animals that are genetically well characterized and inbred at the major histocompatibility complex (MHC). These animals have been used in large animal model studies for many years and have, like their domestic counterparts, very favorable breeding characteristics for being used as donors of organs in xenotransplantation.

A central concern regarding xenotransplantation is the risk of xenosis, infection by organisms transferred with the xenograft into both the transplant recipient and the general population. In particular, "emerging infections" caused by new and previously unknown infectious agents with altered pathogenicity, have to be considered as a potential risk associated with xenotransplantation. The risk of viral infection is increased in transplantation by the presence of factors commonly associated with viral activation, e.g., immune suppression, graft-versus-host disease, graft rejection, viral co-infection, and cytotoxic therapies.

Herpesviruses are the causative agents of many diseases that share a commonality of latency and recurrent infections. Herpesviruses may persist for years in a dormant state and become reactivated after later provocation. While the herpesviruses are widely separated in terms of genomic sequence and proteins, many are similar in terms of virion structure and genome organization. Herpesvirus represents a DNA virus family containing a central icosahedral core of double-stranded DNA. There is a lipoprotein envelope that is trilaminar and 100–200 nm in diameter and a nucleus that is 30–43 nm in diameter. The genome size is large, up to 235 kbp DNA. Based upon the structural and morphological features, the herpesvirus family is divided into three main families: alpha, beta, and gamma. Examples of alpha herpesviruses are herpes simplex and varicella zoster, examples of beta herpesviruses are cytomegalovirus and human herpesvirus 6 while examples of gamma-herpesviruses are Epstein Barr virus and human herpesvirus 8.

Prior to this invention, members of three porcine herpesvirus families had been identified, namely of the alpha, beta, and gamma-herpesvirus families. Suid herpesvirus 1 (SHV1), which causes pseudorabies (PRV) in pigs, is an alpha-herpesvirus and results in neonatal death of piglets, and can be eradicated by vaccination. The glycoprotein II gene of SHV1 is reportedly closely related to the gpB gene of other herpesviruses (Robbins et al. (1987) *J. Virology.* 61:2691–2701). Suid herpesvirus 2 (SHV2), also known as pig cytomegalovirus (pCMV), is found in the respiratory tract of pigs and causes atopic rhinitis, abortion, or neonatal piglet losses. Only the DNA polymerase gene of SHV2 has been reported (Genbank Accession Number AJ222640). Detection of two novel porcine herpesviruses with high similarity to other gamma-herpesviruses were recently reported (Ehlers et al. (1999) *J. General Virology,* 80:971–978), wherein the sequence of the DNA polymerase gene was reported (Genbank Accession Numbers AF118399 and AF118401).

Subsequent examination, as disclosed herein, of pigs for the presence of a gamma-herpesvirus by PCR methods designed to amplify the DNA regions encoding all or part of the glycoprotein B (gpB) envelope molecule has resulted in the detection of sequence similarity to other known gamma-herpesviruses.

BRIEF SUMMARY OF THE INVENTION

It is an object of the present invention to provide isolated polynucleotide sequences encoding a polypeptide that corresponds to a novel porcine gamma-herpesvirus glycoprotein B, herein called pGHV-gpB. Such sequences may be derived from genomic DNA.

It is another object of the present invention to provide immunogenically active fragments and segments of said polynucleotide for use as probes in the detection of similar sequences in related organisms.

A further object of this invention is to use the polypeptides and fragments thereof of the invention to provide a vaccine against porcine gamma-herpesvirus organisms, which vaccine is useful to protect a pig from productive proliferation of this, or related, gamma-herpesvirus organisms.

A still further object of the present invention is to provide antibodies that are capable of binding to an epitope on the porcine gamma-herpesvirus gpB polypeptides, and fragments, of the invention. Such antibodies are useful for diagnosis of the presence of pGHV-gpB polypeptides or as part of a vaccination program.

BRIEF DESCRIPTION OF THE DRAWINGS

FIG. 1 shows the alignment of Glycoprotein-B (gpB) protein sequences from several known gamma-herpesviruses. The following gamma-herpesviruses were used for the analysis: human herpesvirus 8 (HHV8PEP; Genbank accession number AF092928), rhesus monkey rhadinovirus (RHESRHADPEP; Genbank accession number AF029302), murine herpesvirus 68 (MURH68PEP; Genbank accession number U97553), bovine herpesvirus 4 (BOVINEH4PEP; Genbank accession number Z15044), ateline herpesvirus 3 (ATELINEH3PEP; Genbank accession number AF083424), herpesvirus saimiri (SAIMIRIPEP; Genbank accession number X64346), equine herpesvirus 2 (EQH2PEP; Genbank accession number U20824), Epstein-Barr virus (EBVPEP; Genbank accession number V01555), Alcelaphine herpesvirus 1 (ALCELPEP; Genbank accession number AF005370), and equine herpesvirus 5 (EQH5PEP; Genbank accession number AF050671). Degenerate primers were designed for conserved regions (underlined) along with specific primers for Epstein-Barr Virus (EBV) for control and optimization purposes. Such sequences are continued through FIGS. 1(*a*), 1(*b*) and (*c*).

FIG. 2 shows the DNA sequence of the pGHV-gpB gene (SEQ ID NO: 23) that encodes a gamma-herpesvirus gpB polypeptide of the present invention. A fragment of this is shown as SEQ ID NO: 1.

FIG. 3 shows the deduced polypeptide sequence of the pGHV-gpB cDNA shown in FIG. 2 (SEQ ID NO: 24). The amino acids of the sequence are represented by standard one-letter codes. A fragment of this is shown as SEQ ID NO: 2.

FIG. 4 shows a comparison of the nucleic acid sequences of pGHV-gpB and SHV1 and is therefore an illustration of the nucleic acid sequence identity between SEQ ID NO: 1 (a portion of the sequence of FIG. 2) and a portion of Suid herpesvirus 1 (SHV1, Genbank accession number M17321 nucleotides 641–1300). Row 1 (pGHV-gpB DNA) of the compared sequences is SEQ ID NO: 1 (a portion of the sequence of FIG. 2), row 2 is SHV1 (pGHV1 in the figure), nucleotides 641–1300, and row 3 indicates the nucleotides that show identity. Dashes indicate gaps that were inserted in the alignment process to maximize sequence identity.

FIG. 5 is a comparison of the protein sequences of pGHV-gpB and SHV1 and thus an illustration of the identity between the deduced amino acid sequence of SEQ ID NO: 2 (a portion of the sequence of FIG. 3) and SHV1. The amino acids of the sequence are represented by standard one-letter codes. Row 1 of the compared sequences is SEQ ID NO: 2, row 2 is the amino acid sequence of SHV1 (pGHV1; amino acids 491–850) and row 3 indicates the amino acids that show identity. Dashes indicate gaps that were inserted in the alignment process to maximize sequence identity.

FIG. 6 is a comparison of the nucleic acid sequences of pGHV-gpB and SHV2 and illustrates the nucleic acid sequence identity between SEQ ID NO: 1 and a portion of suid herpesvirus 1 (SHV2, Genbank accession number AJ222640). Row 1 of the compared sequences is SEQ ID NO: 1, row 2 is SHV2, and row 3 indicates the nucleotides that show identity. Dashes indicate gaps that were inserted in the alignment process to maximize sequence identity.

FIG. 7 shows a comparison of the protein sequences of pGHV-gpB and SHV2 and illustrates the identity between the deduced amino acid sequence of SEQ ID NO: 2 and that of SHV2. The amino acids are represented by standard one-letter codes. Row 1 of the compared sequences is SEQ ID NO: 2, row 2 is the amino acid sequence of SHV2, and row 3 indicates the amino acids that show identity. Dashes indicate gaps that were inserted in the alignment process to maximize sequence identity.

FIG. 8 is an illustration of the nucleic acid sequence identity between SEQ ID NO:1 and a portion of the porcine gamma-herpesvirus polymerase (AF118399). Row 1 of the compared sequences is SEQ ID NO:1, row 2 is AF118399 and row 3 indicates the nucleotides that show identity. Dashes indicate gaps that were inserted into the alignment process to maximize sequence identity.

FIG. 9 is an illustration of the nucleic acid sequence identity between SEQ ID NO:1 and a portion of the porcine gamma-herpesvirus polymerase (AF118401). Row 1 of the compared sequences is SEQ ID NO:1, row 2 is AF118401 and row 3 indicates the nucleotides that show identity. Dashes indicate gaps that were inserted into the alignment process to maximize sequence identity.

FIG. 10 shows a Blast 2 sequence comparison of the nucleic acid sequence of pGHV-gpB and Acelaphine herpesvirus (GenBank Accession No. AF005370). The vertical lines indicate matches between the two sequences. The upper "Query" sequence represents the gpB nucleotide sequence while the lower "subject" sequence is the Acelaphine herpesvirus sequence. The numbers for the upper sequence correspond to the residue numbers shown for the sequence of FIG. 2 (SEQ ID NO: 23). About 76% of the residues matched.

FIGS. 11(*a*) and (*b*) show a comparison of the protein sequences of pGHV-gpB and Acelaphine herpesvirus (GenBank Accession No. gi/2337975 (AF005370). The amino acids of these sequences are represented by the standard one-letter codes. Row 1 (query) of the compared sequences is the pGHV-gpB while the lower row (the "subject" sequence) is the Acelaphine herpesvirus sequence. The numbers for the upper row correspond to the residue numbers shown in FIG. 3 (SEQ ID NO: 24).

DETAILED DESCRIPTION OF THE INVENTION

In accordance with one aspect of the present invention, there is disclosed herein an isolated polynucleotide which encodes the polypeptide comprising the amino acid sequence of SEQ ID NO: 24, corresponding to the gpB envelope protein of porcine gamma herpesvirus. Also disclosed are fragments of these polynucleotide and polypeptide sequences, especially that of SEQ ID NO:1 (polynucleotide) and SEQ ID NO:2 (polypeptide).

Polynucleotide sequences of the present invention have been isolated from genomic DNA of miniature swine. These sequences show only low sequence similarity with other known porcine herpesvirus sequences (SHV1 and SHV2 and gamma-herpesvirus polymerase gene), including the sequences corresponding to Genbank Accession Numbers M17321, AJ222640, AF118399 and AF118401, respectively.

In accordance with a further aspect of the present invention the nucleic acid sequences of SEQ ID NO: 23, including fragments thereof, may be utilized under stringent hybridization conditions to isolate from porcine tissue by procedures known in the art, DNA sequences corresponding to porcine gamma-herpesvirus gpB regions and for complete porcine gamma-herpesvirus sequences.

Fragments of the polynucleotide sequences of the present invention were used as hybridization probes for a cDNA or DNA library to isolate the full-length gamma-herpesvirus sequence or fragments thereof. Such fragments also find use as probes in identifying other similar sequences of related organisms. Thus, the present invention further provides an isolated porcine gamma-herpesvirus polynucleotide fragment that is capable of stringently hybridizing to a porcine gamma-herpesvirus polynucleotide sequence. In this manner, the present invention provides probes and/or primers for use in ex vivo porcine gamma-herpesvirus detection studies. Typical detection methods involve use of the polymerase chain reaction, sequence analysis, and hybridization techniques. Thus, the present invention also provides pGHV-gpB specific oligonucleotide probes and primers.

The present invention further relates to a method of detecting the presence of gamma herpesvirus in a sample comprising detecting the presence in said sample of a polynucleotide having a sequence at least 80%, preferably at least 90%, most preferably 95% identical to a sequence encoding a polypeptide of the present invention. Said sample may be blood or other tissue sample. The presence of a polypeptide, or immunogenic fragments thereof, of the present invention may also be detected in such samples.

In addition, the present invention also relates to an isolated nucleic acid probe comprising an oligonucleotide whose sequence is at least 95% identical to a fragment, portion or segment of a polynucleotide encoding a polypeptide of the present invention. Such oligonucleotide probe may be either a DNA (i.e., a polydeoxyribonucleotide) or an RNA (i.e., a polyribonucleotide). In a preferred embodiment, said oligonucleotide probe and said fragment have the same sequence.

In a particular embodiment, said isolated nucleic acid probe will comprise an oligonucleotide that is at least 15 nucleotides in length, preferably at least 30 nucleotides in length, most preferably at least 60 nucleotides in length, and especially where said probe is at least 100 nucleotides in length. Such probes commonly hybridize to said oligonucleotides under stringent conditions, as defined herein. SEQ ID NO: 1. In another specific embodiment, the isolated nucleic acid probe oligonucleotide has the sequence of SEQ ID NO: 1.

In a separate embodiment, the isolated nucleic acid probe oligonucleotide of the present invention has a sequence at least 95% identical to the sequence, and is preferably identical to a sequence, selected from the group consisting of the sequences of SEQ ID NO: 25, 26, 27, 28, 29, 30, 31, 32, 33, 34, 35, and 36.

The method of the present invention also provides a means wherein the polynucleotide coding for gpB protein is detected using a probe as disclosed herein. Useful probes also include oligonucleotides whose sequence is selected from the group consisting of SEQ ID NO: 25, 26, 27, 28, 29, 30, 31, 32, 33, 34, 35, and 36.

Porcine gamma-herpesvirus specific oligonucleotides can be detected and/or prepared from the porcine gamma-herpesvirus gpB sequence of the present invention and can be synthesized according to known techniques. They will have substantial sequence identity (e.g., at least 75%, preferably at least 90%, most preferably at least 95%, and most especially 100% sequence identity) with one of the strands (either plus or minus) shown herein (SEQ ID NO: 23, which shows the sense, or plus, or coding, or anti-template strand) or an RNA equivalent, or with part of such a strand, or with a complement thereof.

The present invention further relates to isolated polynucleotides having at least 75% identity to the nucleotide sequence of SEQ ID NO: 23, preferably at least 90% sequence identity thereto, most preferably at least 95% sequence identity thereto, with the preferred embodiment being an isolated polynucleotide comprising the nucleotide sequence of SEQ ID NO: 23.

Likewise, polypeptides comprising the peptides encoded by porcine gamma-herpesvirus sequences are useful for generating antibodies to detect the presence of gamma-herpesvirus polypeptides when they are expressed in porcine tissues. Most useful is the polypeptide sequence of SEQ ID NO:24 (gpB protein) as well as immunogenically active fragments thereof (for example, the fragment whose sequence is that of SEQ ID NO: 2).

The present invention also relates to fragments, portions and segments of the polynucleotides and polypeptides disclosed herein, especially where said fragments, portions or segments are useful as probes (in the case of polynucleotides) or have immunogenic activity (in the case of polypeptides). Polypeptides of the present invention include fragments having at least 30, preferably at least 50, and most preferably at least 70 amino acid residues in common with some portion of the sequence of SEQ ID NO: 24.

"Polynucleotide sequences" as used herein refers to a chain of nucleotides such as deoxyribose nucleic acid (DNA) and transcription products thereof, such as RNA. The polynucleotides of the present invention include DNA, which includes cDNA, genomic DNA, non-genomic DNA, and synthetic DNA, and RNA, such as mRNA present in infected cells.

The term "oligonucleotide" encompasses nucleotides of preferably at least 15 bases (e.g. 15 bases to 600 bases) in length, more preferably 15 bases to 50 bases and most preferably 15 bases to 100 bases.

The term "gene" means the segment of DNA involved in producing a polypeptide chain; it includes regions preceding and following the coding region (leader and trailer sequences) as well as intervening sequences (introns) between individual coding segments (exons).

"Stringent hybridization" or "hybridization under stringent conditions" means hybridization that can be effected at a temperature of between 50° C. and 70° C. in 2×SSC (1×SSC is 17.5 g NaCl, 8.8 g of sodium citrate in 800 ml of $H_2O$, the pH is adjusted to 7.4 with NaOH and the volume adjusted to one liter), containing 0.1% sodium dodecyl sulfate (SDS). In a most preferred embodiment, the sample and probes are sufficiently similar that the hybridization is unaffected by treatment with 0.1×SSC and 0.1% SDS at 65° C. Gamma-herpesvirus gpB specific oligonucleotides can be designed to specifically hybridize to gamma-herpesvirus specific nucleic acids. They can also be synthesized by known techniques and used as primers in PCR (i.e., polymerase chain reaction), or sequencing reactions, or as probes in hybridizations designed to detect the presence of gamma herpesvirus material in a sample. The oligonucleotides may be labeled by suitable labels known in the art, such as radioactive labels, chemiluminescent labels or fluorescent labels and the like.

In accordance with the present invention, the term "Percent Identity" or "Percent Identical", when referring to a sequence, means that a sequence is compared to a claimed or described sequence after alignment of the sequence to be compared (the "Compared Sequence") with the described or claimed sequence (the "Reference Sequence"). The percent identity is then determined according to the following formula:

$$\text{Percent Identity}=100\ [1-(C/R)]$$

wherein C is the number of differences between the Reference Sequence and the Compared Sequence over the length of alignment between the Reference Sequence and the Compared Sequence wherein (i) each nucleotide or amino acid in the Reference Sequence that does not have a corresponding aligned nucleotide or amino acid in the Compared Sequence and (ii) each gap in the Reference Sequence and (iii) each aligned nucleotide or amino acid in the Reference Sequence that is different from an aligned nucleotide or amino acid in the Compared Sequence, constitutes a difference; and R is the number of nucleotides or amino acids in the Reference Sequence over the length of the alignment with the Compared Sequence with any gap created in the Reference Sequence also being counted as a nucleotide or amino acid. If an alignment exists between the Compared Sequence and the Reference Sequence for which the Percent Identity as calculated above is about equal to or greater than a specified minimum Percent Identity then the Compared Sequence has the specified minimum Percent Identity to the Reference Sequence even though alignments may exist in which the hereinabove calculated Percent Identity is less than the specific Percent Identity.

Typically, the melting temperature ($T_m$) of an oligonucleotide less than 30 nucleotides may be calculated according to the formula:

$$T_m=86.35-0.41\ [\%(G+C)]-600/N$$

where N=Chain Length (i.e., number of base pairs)

The present invention also relates to vectors that include the novel polynucleotides (including fragments, segments and portions thereof, as defined below) disclosed herein, host cells which are genetically engineered with or without vectors of the invention to contain said polynucleotides and express said polypeptides, and the synthesis of polypeptides of the invention by recombinant techniques or by direct chemical synthesis.

As used herein, the terms "portion," "segment," and "fragment," when used in relation to polypeptides, refer to a continuous sequence of residues, such as amino acid residues, which sequence forms a subset of a larger sequence. For example, if a polypeptide were subjected to treatment with any of the common endopeptidases, such as trypsin or chymotrypsin, the oligopeptides resulting from such treatment would represent portions, segments or fragments of the starting polypeptide. When used in relation to a polynucleotides, such terms refer to the products produced by treatment of said polynucleotides with any of the common endonucleases or exonucleases.

A polypeptide of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The present invention further relates to a polypeptide which comprises the deduced amino acid sequence of SEQ ID NO: 24, as well as fragments thereof. Preferred are fragments comprising 25 or more consecutive amino acids, more preferred are fragments are fragments with at least 40 amino acids and even more preferred are fragments comprising 50 or more amino acids of the polypeptide of SEQ ID NO: 24. A preferred embodiment is the sequence of SEQ ID NO: 2.

The present invention further relates to variants of the disclosed polynucleotides which encode fragments, including analogs and derivatives, of the polypeptide comprising the amino acid sequence of SEQ ID NO: 24. Such variants may be naturally occurring allelic variants of the polynucleotides or may be non-naturally occurring (for example, variants produced by mutagenesis techniques).

Additional preferred embodiments include polynucleotides encoding gamma herpesvirus polypeptide variants, analogs, derivatives and fragments, and variants, analogs and derivatives of the fragments, which comprise the amino acid sequence of SEQ ID NO:2 in which one or more of the amino acids have optionally been replaced so long as said polypeptide still retains at least 80% identity with the amino acid sequence of SEQ ID NO 24, more preferably 90% sequence identity therewith, most preferably 95% sequence identity therewith and most especially being identical to the sequence of SEQ ID NO: 24, regardless of whether such sequence identities are achieved through addition, deletion, or substitution of amino acid residues.

Especially preferred among these are conservative substitutions, additions and deletions, which do not alter the properties and activities of the gamma herpesvirus gpB polypeptide. Also especially preferred are conservative substitutions. Most highly preferred are mature polypeptides comprising the amino acid sequence set forth in SEQ ID NO: 24 without substitutions.

Thus, the present invention includes polynucleotides encoding polypeptides comprising the sequence of SEQ ID NO: 24 as well as variants of such polynucleotides which variants encode a fragment, derivative or analog of the polypeptides set forth in SEQ ID NO: 24. Such nucleotide variants include deletion variants, substitution variants and addition or insertion variants.

As hereinabove indicated, the polynucleotides may have a coding sequence which is a naturally occurring allelic variant of the coding sequences comprising the coding portion of the polynucleotide sequence shown in FIG. 2 (of SEQ ID NO: 23). As known in the art, an allelic variant is an alternate form of a polynucleotide sequence which may have a substitution, deletion or addition of one or more nucleotides, which does not substantially alter the function of the encoded polypeptide.

The present invention also encompasses polynucleotides which may be fused in the same reading frame to a polynucleotide sequence which aids in expression and secretion of a polypeptide from a host cell, for example, a leader sequence which functions as a secretory or signal sequence for controlling transport of a polypeptide from the cell. The polypeptide having a leader sequence is a pre-protein and may have the leader sequence cleaved by the host cell to form the secreted form of the polypeptide.

The polynucleotides of the present invention may also have the coding sequence fused in frame to a marker sequence which allows for purification of the polypeptides of the present invention. The marker sequence may be a hexa-histidine tag supplied by a pQE-9 vector to provide for purification of the mature polypeptides fused to the marker in the case of a bacterial host, or, for example, the marker sequence may be a hemagglutinin (HA) tag when a mammalian host, e.g. COS7 cells, is used. The HA tag corresponds to an epitope derived from the influenza hemagglutinin protein (Wilson, I., et al. 1984. *Cell* 37:767).

The terms "derivative" and "analog" when referring to the polypeptides comprising the polypeptide as set forth in SEQ ID NO:24, means polypeptides which retain essentially the same biological function or activity as such polypeptides. Thus, an analog includes a pre-protein which can be secreted following cleavage of the pre-protein portion to produce an secretable polypeptide.

The polypeptides of the present invention may be recombinant polypeptides, natural polypeptides or synthetic polypeptides, preferably recombinant polypeptides.

The fragment, derivative or analog of the polypeptides comprising the amino acid sequence set forth in SEQ ID NO: 24 may be one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the polypeptide, such as a leader or secretory sequence or a sequence which is employed for purification of the mature polypeptide or a pre-protein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include polypeptides comprising the polypeptide of SEQ ID NO:2 or a fragment thereof, which fragment may be all or a portion of the polypeptide of SEQ ID NO:2, as well as polypeptides which have at least 80% similarity to such polypeptides, preferably at least 90% similarity, more preferably at least 95% similarity, and most preferably are identical to polypeptides comprising the amino acid sequence of SEQ ID NO:2 and include portions or fragments of such polypeptides with such portion or fragment comprising at least 30 amino acids, preferably at least 40 amino acids and most preferably at least 50 amino acids. Preferred embodiments are fragments comprising 30 or more consecutive amino acids, more preferred are fragments with at least 40 amino acids and even more preferred are fragments comprising 50 or more amino acids of the polypeptide of SEQ ID NO:24, such as SEQ ID NO: 2 (which corresponds to residue numbers 484–678 of SEQ ID NO: 24 (shown in FIG. 3).

As known in the art "similarity" between two polypeptides is determined by comparing the amino acid sequence and its conserved amino acid substitutes of one polypeptide to the sequence of a second polypeptide. For such a determination, two amino acid sequences are compared along a stretch of their sequences, any gap (or gaps) introduced in one sequence to improve the alignment and similarity to the other sequences is counted as spaces of dissimilarity equal to the number of amino acids corresponding to the gap which are present in the second sequence, and the total number of similar amino acids are divided by the total number of amino acids present in the comparison area which counts the spaces of gaps as part of the comparison area.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides, and fragments thereof, of the present invention, host cells which are genetically engineered with vectors of the invention and the production of polypeptides of the invention by recombinant techniques.

Host cells are genetically engineered (transduced or transformed or transfected) with the vectors of the invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli.* lac or trp, the phage lambda PL promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli.*

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli*, Streptomyces, *Salmonella typhimurium*; fungal cells, such as yeast; insect cells such as Drosophila S2 and Spodoptera Sf9 animal cells such as CHO, COS or Bowes melanoma; adenoviruses; plant cells, etc. The selection of an appropriate host is deemed to be within the scope of those skilled in the art from the teachings herein.

More particularly, the present invention relates to recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pBS, pD10, phagescript, psiX174, pBluescript-SK, pBSKS, pNH8A, pNH16a, pNH18A, pNH46A (Stratagene); pTRC99a, pKK2233, pKK233-3, pDR540, pRIT5 (Pharmacia). Eukaryotic: PWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host. Baculovirus systems are especially useful in practicing the present invention.

Promoter regions can be selected from any desired gene using CAT (chloramphenicol transferase) vectors or other vectors with selectable markers. Two appropriate vdctors are pKK232-8 and pCM7. Particular named bacterial promoters include lacI, lacZ, T3, T7, gpt, lambda PRI PL and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE Dextran mediated transfection, or electroporation (Davis, L., Dibner, M., Battey, I., Basic Methods in Molecular Biology, (1986)).

The constructs in host cells can be used in a conventional manner to produce the gene products encoded by the recombinant sequences. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples include the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), alpha-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *Escherichia coli, Bacillus subtilis, Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and pGEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS7 lines of monkey kidney fibroblasts, described by Gluzman (1981) Cell, 23:175, and other cell lines capable of expressing a compatible vector, for example, the C127, 3T3, CHO, HeLa, 293 and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the expressed polypeptide. Finally, high performance liquid chromatography (HPLC) can be employed for final purification steps.

The present invention also relates to diagnostic assays for detecting expression of the gamma-herpesvirus gpB polypeptide in various tissues. Assays used to detect levels of the gamma-herpesvirus gpB polypeptide in a sample derived from a host are well-known to those of skill in the art and include radioimmunoassays, competitive-binding assays, Western Blot analysis, ELISA assays and "sandwich" assay. An ELISA assay (Coligan, et al., Current Protocols in Immunology, 1(2), Chapter 6, (1991)) initially comprises preparing an antibody specific to the gamma-herpesvirus gpB polypeptide antigen, preferably a monoclonal antibody. In addition a reporter antibody is prepared against the monoclonal antibody. To the reporter antibody is attached a detectable reagent such as radioactivity, fluorescence or, in this example, a horseradish peroxidase enzyme. A sample is removed from a host and incubated on a solid support, e.g. a polystyrene dish that binds the proteins in the sample. Any free protein binding sites on the dish are then covered by incubating with a non-specific protein like BSA (bovine serum albumin). Next, the monoclonal antibody is incubated in the dish during which time the monoclonal antibodies attach to gamma-herpesvirus gpB polypeptide attached to the polystyrene dish. All unbound monoclonal antibody is washed out with buffer. The reporter antibody linked, for example, to horseradish peroxidase is then placed in the dish resulting in binding of the reporter antibody to any monoclonal antibody bound to the gamma-herpesvirus gpB polypeptide. Unattached reporter antibody is then washed out. Peroxidase substrates are then added to the dish and the amount of color developed in a given time period is a measurement of the amount of the gamma-herpesvirus gpB polypeptide, or fragments thereof, present in a given volume of sample when compared against a standard curve.

A competition assay may be employed wherein antibodies specific to the gamma-herpesvirus gpB polypeptide, or fragments thereof, are attached to a solid support, labeled gamma-herpesvirus gpB polypeptide and a sample derived from the host are passed over the solid support, and the amount of label detected. The label can be detected, for example, by liquid scintillation chromatography and can be correlated to a quantity of the gamma-herpesvirus gpB polypeptide present in the sample.

A "sandwich" assay is similar to an ELISA assay. In a "sandwich" assay the gamma-herpesvirus gpB polypeptide, or a suitable fragment thereof, is passed over a solid support and binds to antibody attached to a solid support. A second antibody is then bound to the gamma-herpesvirus gpB polypeptide. A third antibody which is labeled and specific to the second antibody is then passed over the solid support and binds to the second antibody and an amount can then be quantified.

The present invention also relates to compositions comprising immunogenic polypeptides, and active fragments thereof, disclosed according to the invention. Where intended for use in a clinical setting, such compositions will commonly contain the polypeptides, and active fragments thereof, suspended in a pharmacologically acceptable diluent or excipient.

The present invention further relates to the use of such compositions as vaccines, wherein said vaccines comprise immunogenically effective amounts of said compositions. Additionally, the invention contemplates a method of vaccinating a pig against a porcine, or swine, gamma-herpesvirus by administering to said pig the vaccine of the present invention.

The present invention also relates to a method of immunizing an animal, especially a pig, against a porcine gamma-herpesvirus, comprising administering to said pig an isolated polynucleotide encoding a polypeptide (or immunogenically active fragments thereof) according to the invention, such that the encoded polypeptide is eventually expressed in an immunogenically effective amount.

Pharmaceutical compositions, such as those designed to vaccinate, or otherwise induce active immunity, may be administered in a convenient manner such as by topical, intravenous, intraperitoneal, intramuscular, intratumor, subcutaneous, intranasal or intradermal routes. Such pharmaceutical compositions are administered in an amount which is effective for treating and/or prophylaxis of the specific indication.

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of a Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptide itself. In this manner, even a sequence encoding only a fragment of the polypeptide can be used to generate antibodies binding the whole native polypeptide. Such antibodies can then be used to isolate the polypeptide from tissue expressing that polypeptide.

Antibodies specific to the polypeptide of the present invention may be employed as a diagnostic to determine the presence of a gamma-herpesvirus in tissue, which gamma herpesvirus expresses the gpB polypeptide (or a related polypeptide) in a sample derived from a host by techniques known in the art. Such antibodies may be useful to provide passive immunity in a host.

More specifically, the present invention relates to a method for creating, or otherwise producing or inducing, passive immunity in a pig comprising administering to said pig an immunogenically effective amount of one or more antibodies specific for the polypeptides, or fragments thereof, disclosed herein.

For preparation of monoclonal antibodies, any technique which provides antibodies produced by continuous cell line cultures can be used. Examples include the hybridoma technique (Kohler and Milstein (1975) *Nature,* 256:495–497), the trioma technique, the human B-cell hybridoma technique (Kozbor et al. (1983) *Immunology Today* 4:72), and the EBV-hybridoma technique to produce human monoclonal antibodies (Cole et al. (1985) in Monoclonal *Antibodies and Cancer Therapy*, Alan R. Liss, Inc., pp. 77–96), to mention only a few. Newer technologies present no obstacles to practicing the present invention.

Antibodies specific for the polypeptides disclosed herein may also be generated by genetically engineered cells transformed by the introduction into the genome of said cells, or by introduction of non-integrating vectors into said cells, of either polynucleotides alone, or vectors containing said polynucleotides, coding for said antibodies.

Techniques described for the production of single chain antibodies (U.S. Pat. No. 4,946,778) can be adapted to produce single chain antibodies to immunogenic polypeptide products of this invention.

Such antibodies to the polypeptides of the present invention may be utilized to detect the presence or the absence of the polypeptides of the present invention. Thus, they are useful in an assay to verify the successful insertion of the polynucleotides of the present invention (as part of a construct) into a host cell. Thus, the protein encoded by the inserted polynucleotide according to the present invention, when expressed by the transformed host cell, serves as a "marker" for the successful insertion of the polynucleotide that can be detected by an antibody for the marker.

In general, antibodies against the polypeptides will be administered in an amount of at least about 10 mg/kg body weight and in most cases they will be administered in an amount not in excess of about 8 mg/kg body weight per day. In most cases, the dosage is from about 1 mg/kg to about 10 mg/kg body weight daily, taking into account the routes of administration, symptoms, etc.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 $\mu$g of plasmid, or DNA fragment is used with about 2 units of enzyme in about 20 $\mu$l of buffer solution. For the purpose of isolating DNA fragments for plasmid construction, typically 5 to 10 $\mu$g of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

General procedures useful in practicing the methods disclosed herein can be found in, for example, Sambrook et al., Molecular Cloning: A Laboratory Manual, Second Edition, Cold Spring Harbor, N.Y., (1989), Wu et al, *Methods in Gene Biotechnology* (CRC Press, New York, N.Y., 1997), and *Recombinant Gene Expression Protocols*, in Methods in *Molecular Biology*, Vol. 62, (Tuan, ed., Humana Press, Totowa, N.J., 1997), the disclosures of which are hereby incorporated by reference.

"Ligation" refers to the process of forming phosphodiester bonds between two double stranded nucleic acid fragments (See Sambrook et al, supra).

In carrying out the procedures of the present invention it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

The present invention will be further described with reference to the following examples; however, it is to be understood that the present invention is not limited to such examples. All parts or amounts, unless otherwise specified, are by weight. In order to facilitate understanding of the invention the following examples providing certain frequently occurring methods and/or terms will be described.

EXAMPLE 1

Isolated and Sequence Analysis of Porcine Gamma-Herpesvirus Glycoprotein B Gene Sequences Primers: Primers were synthesized for use in the amplification of pGHV-gpB gene sequences. Alignment of gpB protein sequences from several known gammaherpesviruses (FIG. 1) showed that there are four conserved regions (identified by underlining). Degenerate primers corresponding to these regions were synthesized (Table 1).

TABLE 1

| | | |
|---|---|---|
| R = A or G | Y = C or T | M = A or C |
| K = G or T | S = G or C | W = A or T |
| H = A or T or C | B = G or T or C | D = G or A or T |
| N = A or G or C or T | V = G or A or C | I = Inosine |

F and R indicate whether the primers were in the sense or antisense direction respectively.

| Degenerate Primers | Polypeptide Sequence | Sequence (5' to 3') |
|---|---|---|
| RTT-F1 | Includes sequence RTTVNC | MGA ACA ACI GTY AAY TGY GA |
| RTT-F2 | Includes sequence RTTVNC | MGA ACA ACI GTY AAY TGY CT |
| RTT-F3 | Includes sequence RTTVNC | MGA ACA ACI GTY AAY TGY |
| QLIV-F4 | Includes sequence QXQF/YAY | CAR ITI CAR TWT GCM TAY GAC |
| QLIV-F5 | Includes sequence QXQF/YAY | CAR ITI CAR TWT GCM TAY G |
| NPTV-F6 | Includes sequence VMXS/T/AY | GTB ATG WSH AGV ATH TAY GG |
| NPTV-F7 | Includes sequence VMXS/T/AY | GTB ATG WSH GCV ATH TAY GG |
| NPTV-R1 | | SWC ATI ACR STI GTI GGR TT |
| FREYN-R3 | Includes sequence FREYN | TR IGY GTA RTA RTT RTA YTC YCT RAA |
| FREYN-R4 | Includes sequence FREYN | GTA RTA RTT RTA YTC YCT RAA |
| FREYN-R5 | Includes sequence FREYN | CTG RAA RTT RTA YTC YCG RAA |
| FREYN-R6 | Includes sequence FREYN | TG IGY CTG RAA RTT RTA YTC YCG RAA |

Primers were also designed to Epstein-Barr virus (EBV) for control and assay optimization purposes (Table 2). Primer names ending with an "F" are sense strand primers, primer names ending with an "R" are anti-sense strand primers.

TABLE 2

| Epstein-Barr Virus Control Primers | Similar to: | Sequence (5' to 3') |
|---|---|---|
| EBV-F2 | RTT-F2 | AGA ACT ACC GTC AAC TGC CT |
| EBV-F3 | RTT-F3 | AGA ACT ACC GTC AAC TGC |
| EBV-F4 | QLIV-F4 | CAG ATC CAA TTT GCC TAC GAC |
| EBV-F5 | QLIV-F5 | CAG ATC CAA TTT GCC TAC G |
| EBV-F6 | NPTV-F6 | GTC ATG TCC AGC ATC TAC GG |
| EBV-R1 | NPTV-R1 | GAC ATG ACG GTG GTT GGA TT |
| EBV-R3 | FREYN-R3 | TGC GCC TGG AAG TTG TAC TCC CGG AA |
| EBV-R5 | FREYN-R5 | CTG GAA GTT GTA CTC CCG GAA |

Oligonucleotides used to sequence the pGHV gpB gene were as follows:

| Sequencing Primers | Sequence (5' to 3') | Hybridizes To: |
|---|---|---|
| -47 Sequencing Primer | CGC CAG GGT TTT CCC AGT CAC GAC | TOPO-pCRII: bases 434—458 |
| M13 Reverse | CAG GAA ACA GCT ATG AC | TOPO-pCRII: bases 205—222 |
| TEF-14 | CAG GGA CGA GAA GAG GCT TA | pGHV gpB: bases 1989—2008 |
| TER-22 | ACA CCA GAG CAG CTC TAT G | pGHV gpB: bases 1513—1531 |
| TEF-23 | TAG CAC CAA TCA GTG AAG AAG AGC | pGHV gpB: bases 2399—2422 |
| TEF-24 | GCC AGT GAT ATG GTA CAC AGT G | pGHV gpB: bases 322—343 |
| TEF-25 | TAA CAG GTC ACT ATG GAA CAC ACG | pGHV gpB: bases 140—163 |
| TEF-26 | TTC TTT AAG ACT AAA CAC AGG TGG | pGHV gpB: bases 537—560 |
| TEF-27 | GGA GTG GTG AAG ATG ATC ATG | pGHV gpB: bases 815—835 |
| TER-28 | CCA TAA TGT TAG TGG ACA ATA TGA C | pGHV gpB: bases 993—1017 |
| TER-29 | ATG ACG CTG TGA TGT CAT TGG | pGHV gpB: bases 1073—1093 |
| TER-30 | GAT GCA CTG AGA AGC CTG AGA C | pGHV gpB: bases 1673—1694 |

Isolation and Sequence Analysis of Porcine Gamma-Herpesvirus Glycoprotein B

Equal amounts of genomic DNA from miniature swine #13432 and #13433 were pooled together. These animals (a/d haplotype) had been the recipients of bone marrow or stem cells from a/c haplotype animals and had been given cyclosporine treatment. The animals had both developed a lymphoma. Genomic DNA was extracted using Qiagen, Inc.'s QIAmp® Blood Kit (Chatsworth, Calif.). One hundred ng of the DNA pool was added to each polymerase chain reaction (PCR) tube along with reagents. The final 50 µl reaction mixtures included 25 mM KC1, 10 mM Tris-HCl (pH 8.3), 3.5 mM $MgCl_2$ (Stratagene, Los Angeles, Calif.), 0.2 mM DNTP and 2.5 units of Amplitaq Gol® DNA polymerase (Perkin-Elmer Corporation, Philadelphia, Pa.). Several different combinations of forward and reverse primers were used (20 pmoles of each primer per reaction). These are summarized as follows:

| Forward Primer | Reverse Primer |
|---|---|
| QLIV-F4 | FREYN-R5 |
| EBV-F4 | FREYN-R5 |
| QLIV-F4 | EBV-R5 |
| QLIV-F4 | FREYN-R6 |
| QLIV-F5 | FREYN-R5 |
| EBV-F5 | FREYN-R5 |
| QLIV-F5 | EBV-R5 |
| QLIV-F5 | FREYN-R6 |
| EBV-F4 | FREYN-R3 |
| EBV-F4 | FREYN-R4 |
| QLIV-F4 | FREYN-R3 |
| QLIV-F4 | FREYN-R4 |
| QLIV-F5 | FREYN-R3 |
| QLIV-F5 | FREYN-R4 |

The reactions were amplified in a Perkin-Elmer GeneAmp® 9600 thermal cycler. The initial denaturing step was 9 minutes at 95° C. (required to activate the "hot-start" Amplitaq Gold®) followed by 30 cycles of 94° C. for 30 seconds, 45° C. for 60 seconds and 72° C. for 60 seconds. Thermal cycling was followed by a 5 minutes incubation at 72° C. and brought down to 4° C.

The PCR products were visualized on a 2% agarose gel stained with ethidium bromide. PCR products were visible using the following primer pairs: QLIV-F5/FREYN-R6, EBV-F4/FREYN-R4, QLIV-F4/FREYN-R4, QLIV-F5/FREYN-R3. The sizes of the product varied from approximately 350 base pairs to 800 base pairs (expected size of the product was approximately 600 base pairs). The PCR products were purified using Microspin G-50® columns (Amersham Pharmacia Biotech, Newark, N.J.) and TA-ligated into the PCRII-TOPO® vector (Invitrogen Corp., San Diego, Calif.). The ligation reactions were then transformed into competent TOP10F' *E.coli* supplied by Invitrogen Corp. The cells were incubated on carbenicillin (Sigma Chemical Company, St. Louis, Mo.)/IPTG/X-gal (Amresco, Inc., Solon Ohio) agar plates and selected colonies were grown up in LB broth (Gibco Life Technologies, Baltimore, Md.). Plasmid DNA was extracted using the Wizard® miniprep kit (Promega Corp., Madison, Wis.). EcoRI (New England Biolabs, Beverly, Mass.) restriction digests of the minipreps were electrophoresed on a 2% agarose gel to determine the insert size.

In order to screen for herpesvirus sequences, miniprep DNA from the clones was hybridized to an EBV probe in a slot-blot array. Miniprep DNA (1 μl of each sample tested) was denatured by adding NaOH followed by a 10 minute incubation at 96° C. The samples were then added to GeneScreen® membrane (NEN Life Sciences, Pittsburgh, Pa.) inserted in a Minifold II® slot-blot apparatus (Schleicher & Schuell, Keene, N.H.). The blot was removed and crosslinked using a UV Stratalinker 1800® (Stratagene). EBV PCR product was generated from an EBV-transformed human B cell line (721.221, ATCC CRL 1855) using similar reagents and conditions as the previous PCR and with EBV-F4 and EBV-R5 primers. The PCR product was denatured and added to the Ready-to-go Beads® random priming kit (Amersham Pharmacia Biotech, Newark, N.J.) with $^{32}$p dCTP (NEN Life Sciences). Approximately $1\times10^6$ CPM of probe in 10 ml of ExpressHyb® hybridization solution (Clontech Laboratories, Inc., Palo Alto, Calif.) was added to a tube containing the slot-blot membrane and incubated at 60° C. for 90 minutes. The probe was then removed and the membrane was washed twice for 10 minutes with 6×SSC at 60° C. 8×10" Fuji RX film (Fisher Scientific, Pittsburgh, Pa.) was exposed to the blot overnight and developed. Several clones from the PCRs using EBV-F4/FREYN-R4 primers and QLIV-F4/FREYN-R4 hybridized to the EBV probe. Clones from other primer pairs as well as a QLIV-F4/FREYN-R4 clone with a uniquely small insert did not hybridize to the probe. Three EBV-F4/FREYN-R4 EBV-positive clones and three QLIV-F4/FREYN-R4 EBV-positive clones were selected for DNA sequencing. The DNA sequencing analysis was performed by Lark Technologies, Inc (Houston, Tex.). The DNA sequence obtained is shown in FIG. 2. The hypothetical protein sequence for the fragment of pGHV-gpB is presented in FIG. 3. The sequences were analyzed using the National Center for Biotechnology Information's BLAST database search program accessible via the internet at www.ncbi.nlm.nih-.gov.BLAST (Altschul et al., 1997). pGHV-gpB was most closely aligned to Alcelaphine (wildebeest) herpesvirus 1 L-DNA (Genbank Accession Number AF005370). Comparison of pGHV-gpB sequence to SHV1 and SHV2 sequences indicated only low sequence similarity at either the nucleic acid of protein levels (FIGS. 4–7). FIGS. 8 and 9 show a comparison of the nucleic acids sequences of SEQ ID NO:1 and a portion of the porcine gamma herpesvirus polymerase (AF118399 and AF118401). FIG. 10 shows a Blast 2 sequence comparison of the nucleic acid sequence of pGHV-gpB and Acelaphine herpesvirus (AF005370). FIG. 11 shows a comparison of the protein sequences of pGHV-gpB and Acelaphine herpesvirus (AF005370).

What is claimed is:

1. An isolated polynucleotide comprising a nucleotide sequence encoding a polypeptide at least 80% identical to the amino acid sequence of SEQ ID NO: 24, wherein the encoded polypeptide binds with antibodies induced by porcine gamma herpesvirus.

2. The isolated polynucleotide of claim 1 wherein said polypeptide is at least 90% identical to the amino acid sequence of SEQ ID NO: 24.

3. The isolated polynucleotide of claim 1 wherein said polypeptide is at least 95% identical to the amino acid sequence of SEQ ID NO: 24.

4. The isolated polynucleotide of claim 1 wherein said polypeptide has the amino acid sequence of SEQ ID NO: 24.

5. The isolated polynucleotide of claim 1 wherein said polypeptide comprises the amino acid sequence of SEQ ID NO: 2.

6. The isolated polynucleotide of claim 1 wherein said polypeptide encodes at least one immunogenic fragment of porcine gamma herpesvirus gpB polypeptide having SEQ ID NO: 24.

7. An isolated polynucleotide comprising a nucleotide sequence encoding a fragment of SEQ ID NO: 24 wherein said fragment comprises at least 80% of SEQ ID NO: 24.

8. The isolated polynucleotide of claim 7 wherein said fragment comprises at least 90% of SEQ ID NO. 24.

9. The isolated polynucleotide of claim 7 wherein said fragment comprises at least 95% of SEQ ID NO. 24.

10. An isolated polynucleotide selected from the group consisting of the complements of the polynucleotides of any of claim 1, 2, 3, 4, 5, 6, 7, 8 or 9.

11. An isolated polynucleotide comprising a nucleotide sequence at least 95% identical to SEQ ID NO: 23.

12. The isolated polynucleotide of claim 11 wherein said nucleotide sequence is the sequence of SEQ ID NO: 23.

13. An isolated polynucleotide comprising a fragment of SEQ ID NO: 23 wherein said fragment encodes at least one immunoreactive fragment of porcine gamma herpesvirus gpB.

14. An isolated polynucleotide comprising the sequence of SEQ ID NO: 1.

15. A recombinant vector comprising a polynucleotide encoding a polypeptide at least 80% identical to the amino acid sequence of SEQ ID NO: 24, wherein the encoded polypeptide reacts with antibodies induced by porcine gamma herpesvirus.

16. A genetically engineered cell comprising a vector of claim 15.

17. A process for detecting the presence of gamma herpesvirus in a sample comprising contacting a first polynucleotide of claim 1, 2, 3, 4, 5, 6, 7, 8, 9, 10, 11, 12, 13 or 14 with a second polynucleotide derived from said sample whereby hybridization of said first and second polynucleotides under stringent conditions indicates the presence of gamma herpes virus in said sample.

18. An isolated nucleic acid probe comprising at least 15 contiguous nucleotides of SEQ ID NO: 23 wherein said probe hybridizes under stringent conditions to the genome of porcine gamma herpesvirus.

19. The isolated nucleic acid probe of claim 18 wherein said oligonucleotide is at least 30 contiguous nucleotides in length.

20. The isolated nucleic acid probe of claim 18 wherein said oligonucleotide is at least 60 contiguous nucleotides in length.

21. The isolated nucleic acid probe of claim 18 wherein said oligonucleotide is at least 100 nucleotides in length.

22. The isolated nucleic acid probe of claim 18 wherein said oligonucleotide is an oligodeoxyribonucleotide.

23. The isolated nucleic acid probe of claim 18 wherein said probe comprises ribonucleotides.

24. The isolated nucleic acid probe of claim 18 wherein said oligonucleotide contains both ribonucleotides and deoxyribonucleotides.

25. A process for detecting the presence of gamma herpesvirus in a sample comprising contacting a probe of claim 18, 19, 20, 21, 22, 23 or 24 with a polynucleotide derived from said sample whereby hybridization of said probe to said polynucleotide under stringent conditions indicates the presence of gamma herpes virus in said sample.

* * * * *

UNITED STATES PATENT AND TRADEMARK OFFICE

CERTIFICATE OF CORRECTION

PATENT NO. : 6,461,811 B1 Page 1 of 1
DATED : October 8, 2002
INVENTOR(S) : Clive Patience It is certified that error appears in the above-identified patent and that said Letters Patent is hereby corrected as shown below:

Column 8,
Line 13, delete “are fragments are fragments” and insert therefor -- are fragments --

Column 18,
Line 63, delete “DNTP” and insert therefor -- dNTP --

Column 20,
Line 13, delete “$^{32}$p” and insert therefor -- $^{32}$P --

Signed and Sealed this

Eighteenth Day of March, 2003

JAMES E. ROGAN
*Director of the United States Patent and Trademark Office*

SEQUENCE LISTING

```
<160> NUMBER OF SEQ ID NOS: 36

<210> SEQ ID NO 1
<211> LENGTH: 585
<212> TYPE: DNA
<213> ORGANISM: Artificial Sequence
<220> FEATURE:
<223> OTHER INFORMATION: Description of Artificial Sequence:Fragment
      from swine gamma Herpesvirus DNA coding for
      glycoprotein B envelope protein

<400> SEQUENCE: 1

aatcttcgta tcagaataaa taacattttg gaagatttgt caaaggcatg gtgtcgtgag     60
```

-continued

```
cagcatagag ctgctctggt gtggaatgag ctcagcaaga ttaatcccac aagcgtcatg    120

agcatgattt acaatagacc cgtatcagcc aaaagaatag gagatgtcat ttcagtctct    180

aactgtattg tggtagacca aaccagtgtc tcattacata aaagtctcag gcttctcagt    240

gcatcggatg aaaagtgctt ctctagacct ccagtgacat ttaagtttat gaatgacagt    300

actatttaca aagggcaact aggagtcaat aatgagattc tcttaaccac aacatacctt    360

gaaacatgtc aggaaaacac tgagtattac tttcaggcaa agacagacat gtacatttac    420

aaaaactatg agcatttgaa gactgtgcct ttatcttcga tcaccacact agatacattt    480

atagccctta attttacact attggagaat gttgacttta aagtcattga actttatacc    540

agggacgaga agaggcttag taatgtcttt gacattgaaa caatg                    585
```

```
<210> SEQ ID NO 2
<211> LENGTH: 195
<212> TYPE: PRT
<213> ORGANISM: Artificial Sequence
<220> FEATURE:
<223> OTHER INFORMATION: Description of Artificial Sequence:Deduced
      amino acid sequence derived from the first open reading
      frame of the DNA of SED ID NO:1

<400> SEQUENCE: 2

Asn Leu Arg Ile Arg Ile Asn Asn Ile Leu Glu Asp Leu Ser Lys Ala
  1               5                  10                  15

Trp Cys Arg Glu Gln His Arg Ala Ala Leu Val Trp Asn Glu Leu Ser
             20                  25                  30

Lys Ile Asn Pro Thr Ser Val Met Ser Met Ile Tyr Asn Arg Pro Val
         35                  40                  45

Ser Ala Lys Arg Ile Gly Asp Val Ile Ser Val Ser Asn Cys Ile Val
     50                  55                  60

Val Asp Gln Thr Ser Val Ser Leu His Lys Ser Leu Arg Leu Leu Ser
 65                  70                  75                  80

Ala Ser Asp Glu Lys Cys Phe Ser Arg Pro Pro Val Thr Phe Lys Phe
                 85                  90                  95

Met Asn Asp Ser Thr Ile Tyr Lys Gly Gln Leu Gly Val Asn Asn Glu
            100                 105                 110

Ile Leu Leu Thr Thr Thr Tyr Leu Glu Thr Cys Gln Glu Asn Thr Glu
        115                 120                 125

Tyr Tyr Phe Gln Ala Lys Thr Asp Met Tyr Ile Tyr Lys Asn Tyr Glu
    130                 135                 140

His Leu Lys Thr Val Pro Leu Ser Ser Ile Thr Thr Leu Asp Thr Phe
145                 150                 155                 160

Ile Ala Leu Asn Phe Thr Leu Leu Glu Asn Val Asp Phe Lys Val Ile
                165                 170                 175

Glu Leu Tyr Thr Arg Asp Glu Lys Arg Leu Ser Asn Val Phe Asp Ile
            180                 185                 190

Glu Thr Met
        195


<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence:PCR
      amplification primer for pGHV-gpB gene sequences

<400> SEQUENCE: 3
```

-continued mgaacaacgt yaaytgyga 19

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence:PCR amplification primer for pGHV-gpB gene sequences

<400> SEQUENCE: 4
mgaacaacgt yaaytgyct 19

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence:PCR amplification primer for pGHV-gpB gene sequences

<400> SEQUENCE: 5
mgaacaacgt yaaytgy 17

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence:PCR amplification primer for pGHV-gpB gene sequences

<400> SEQUENCE: 6
cartcartwt gcmtaygac 19

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence:PCR amplification primer for pGHV-gpB gene sequences; n=i

<400> SEQUENCE: 7
carntncart wtgcmtayg 19

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:PCR amplification primer for pGHV-gpB gene sequences

<400> SEQUENCE: 8
gtbatgwsha gvathtaygg 20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:PCR amplification primer for pGHV-gpB gene sequences

<400> SEQUENCE: 9

-continued

```
gtbatgwshg cvathtaygg                                                   20


<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:PCR
      amplification primer for pGHV-gpB gene sequences;
      n=i

<400> SEQUENCE: 10

swcatnacrs tngtnggrtt                                                   20


<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence:PCR
      amplification primer for pGHV-gpB gene sequences;
      n=i

<400> SEQUENCE: 11

trngygtart arttrtaytc yctraa                                            26


<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence:PCR
      amplification primer for pGHV-gpB gene sequences

<400> SEQUENCE: 12

gtartarttr taytcyctra a                                                 21


<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence:PCR
      amplification primer for pGHV-gpB gene sequences

<400> SEQUENCE: 13

ctgraarttr taytcycgra a                                                 21


<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence:PCR
      amplification primer for pGHV-gpB gene sequences;
      n=i

<400> SEQUENCE: 14

tgngyctgra arttrtaytc ycgraa                                            26


<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence:PCR
      amplification primer for Epstein-Barr Virus genome
```

-continued

<400> SEQUENCE: 15
agaactaccg tcaactgcct 20

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence:PCR amplification primer for Epstein-Barr Virus genome

<400> SEQUENCE: 16
agaactaccg tcaactgc 18

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence:PCR amplification primer for Epstein-Barr Virus genome

<400> SEQUENCE: 17
cagatccaat ttgcctacga c 21

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence:PCR amplification primer for Epstein-Barr Virus genome

<400> SEQUENCE: 18
cagatccaat ttgcctacg 19

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence:PCR amplification primer for Epstein-Barr Virus genome

<400> SEQUENCE: 19
gtcatgtcca gcatctacgg 20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence:PCR amplification primer for Epstein-Barr Virus genome

<400> SEQUENCE: 20
gacatgacgg tggttggatt 20

<210> SEQ ID NO 21
<211> LENGTH: 26
<212> TYPE: DNA
<213> ORGANISM: Artificial Sequence
<220> FEATURE:
<223> OTHER INFORMATION: Description of Artificial Sequence:PCR amplification primer for Epstein-Barr Virus genome -continued

<400> SEQUENCE: 21
tgcgcctgga agttgtactc ccggaa 26

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence:PCR amplification primer for Epstein-Barr Virus genome

<400> SEQUENCE: 22
ctggaagttg tactcccgga a 21

<210> SEQ ID NO 23
<211> LENGTH: 2598
<212> TYPE: DNA
<213> ORGANISM: Artificial Sequence
<220> FEATURE:
<223> OTHER INFORMATION: Description of Artificial Sequence:cDNA for porcine gamma herpesvirus gpB gene

<400> SEQUENCE: 23
atggcaggta gcttaaaact taggggatct gttctagcac tgtggtacct gtatcaggtg 60
gctctttatt cacttagtat agcagagacc ggtgtaacct cacctccaaa tacagcgacc 120
tggtctactg aatcgccgct aacaggtcac tatggaacac acgattcaag ccatggtgaa 180
agaggaaaca acgaaaacag agattcagaa gagcaaaata aaaacattta tggatcgcct 240
tctacgtttc cttacagagt atgcagtgcc tccggagttg gagatgtctt tagatttcag 300
accgaccatg tgtgtcccga tgccagtgat atggtacaca gtgaggggat tctactaatt 360
tacaaacaga acattattcc atttatgttt agagttagga aatatagaaa agttgttaca 420
acaagtactg tctacaatgg tatttattct gactctatta ccaaccaaca tactttctat 480
aaatcaatcg aaccttggga gacagaaaag atggacacaa tatatcagtg ttttaattct 540
ttaagactaa acacaggtgg aaatctgctt acttatgtag atagagatga tataaatatg 600
acagtgtttc tgcaacctgt tgacggtgtg acgcccgatg tgaagaggta tggcagtcaa 660
ccagagctgt accttgaacc tggctggttt tggggtagtt atagaagacg aactacagtg 720
aactgtgaac taatggacat gtttgcaaga tcaaatcctc catttgattt ctttgttaca 780
gctacaggtg atacggtgga aatgtctcca ttttggagtg gtgaagatga tcatgaaaat 840
aagatgcacg agaagccatg gtttgttagt gtgataaata actacaaggt ggtggactat 900
caaaacagag ggactgtacc ccttggaaaa acaaggatat ttctagatag ggaagagtat 960
acattatctt gggaaaagca tctaaaaaat atgtcatatt gtccactaac attatggaaa 1020
gcattttaca atggaatcca gacggagcat tcaggctcat atcattttgt agccaatgac 1080
atcacagcgt cattcacaac tagtaaagaa gacatgaaag agttcaatac gacatatcat 1140
tgtctcaacg aggaaataaa ggcagaaata gagaagaaat atgcaaaagt aaactcaact 1200
cactctaaat atggagatct gaaatacttt aaaacagatg gggtctcta tttagtctgg 1260 caacctctta ttcaaaacag gcttcttgat gctaagaaca aactgaacaa tgagacttat 1320
tccaggagat cacgacgtca ggcagaatct actactgacc caatgatgga gatgactgga 1380
aatggagcag gtggagaata tagcagtgaa aattcaatca cggtggcgca ggtgcagtat 1440
gcctatgaca atcttcgtat cagaataaat aacattttgg aagatttgtc aaaggcatgg 1500
tgtcgtgagc agcatagagc tgctctggtg tggaatgagc tcagcaagat taatcccaca 1560

-continued agcgtcatga gcatgattta caatagaccc gtatcagcca aaagaatagg agatgtcatt 1620
tcagtctcta actgtattgt ggtagaccaa accagtgtct cattacataa aagtctcagg 1680
cttctcagtg catcggatga aaagtgcttc tctagacctc cagtgacatt taagtttatg 1740
aatgacagta ctatttacaa agggcaacta ggagtcaata atgagattct cttaaccaca 1800
acataccttg aaacatgtca ggaaaacact gagtattact ttcaggcaaa gacagacatg 1860
tacatttaca aaaactatga gcatttgaag actgtgcctt tatcttcgat caccacacta 1920
gatacattta tagcccttaa ttttacacta ttggagaatg ttgactttaa agtcattgaa 1980
ctttatacca gggacgagaa gaggcttagt aatgtctttg acattgaaac aatgtttagg 2040
gaatataact actatgctca gagggtcagt ggcctcagaa aggatttgct ggatctaagc 2100
accaatagaa atcaatttgt ggatgcattt ggtagtctta tggatgattt gggtgctgtt 2160
gggcagacag ttgtaaatgc tgtaagtggt gtggctacgc tgtttagctc aattgtaaca 2220
ggatttatta atttcattaa aaacccattt ggtggaatgt taatgattat tgttgttatt 2280
ggtgtgctat ttgccatcta ctttctgacc aaaaagacga agatatatga gacggcaccg 2340
attaagatga tttatcctga aattgacaag ctgaaagaac gtgagggaaa atcagaaata 2400
gcaccaatca gtgaagaaga gctggagaga attgtacttg ctatgcacat ccatcaacaa 2460
aattcacata tggaaacaaa aacaaggaag gatcccaaag acagcatatt aacaagggca 2520
caaaatatgc tacgcaaaag atcaggatat tctaatttaa aaaatgctga atctgtggag 2580
atgttaaaca ctttataa 2598

<210> SEQ ID NO 24
<211> LENGTH: 865
<212> TYPE: PRT
<213> ORGANISM: Artificial Sequence
<220> FEATURE:
<223> OTHER INFORMATION: Description of Artificial Sequence:Deduced amino acid sequence of porcine gamma herpesvirus gpB gene

<400> SEQUENCE: 24

Met Ala Gly Ser Leu Lys Leu Arg Gly Ser Val Leu Ala Leu Trp Tyr
1 5 10 15

Leu Tyr Gln Val Ala Leu Tyr Ser Leu Ser Ile Ala Glu Thr Gly Val
20 25 30

Thr Ser Pro Pro Asn Thr Ala Thr Trp Ser Thr Glu Ser Pro Leu Thr
35 40 45

Gly His Tyr Gly Thr His Asp Ser Ser His Gly Glu Arg Gly Asn Asn
50 55 60

Glu Asn Arg Asp Ser Glu Glu Gln Asn Lys Asn Ile Tyr Gly Ser Pro
65 70 75 80

Ser Thr Phe Pro Tyr Arg Val Cys Ser Ala Ser Gly Val Gly Asp Val
85 90 95

Phe Arg Phe Gln Thr Asp His Val Cys Pro Asp Ala Ser Asp Met Val
100 105 110

His Ser Glu Gly Ile Leu Leu Ile Tyr Lys Gln Asn Ile Ile Pro Phe
115 120 125

Met Phe Arg Val Arg Lys Tyr Arg Lys Val Val Thr Thr Ser Thr Val
130 135 140

Tyr Asn Gly Ile Tyr Ser Asp Ser Ile Thr Asn Gln His Thr Phe Tyr
145 150 155 160

-continued

```
Lys Ser Ile Glu Pro Trp Glu Thr Glu Lys Met Asp Thr Ile Tyr Gln
                165                 170                 175

Cys Phe Asn Ser Leu Arg Leu Asn Thr Gly Gly Asn Leu Leu Thr Tyr
            180                 185                 190

Val Asp Arg Asp Asp Ile Asn Met Thr Val Phe Leu Gln Pro Val Asp
        195                 200                 205

Gly Val Thr Pro Asp Val Lys Arg Tyr Gly Ser Gln Pro Glu Leu Tyr
    210                 215                 220

Leu Glu Pro Gly Trp Phe Trp Gly Ser Tyr Arg Arg Arg Thr Thr Val
225                 230                 235                 240

Asn Cys Glu Leu Met Asp Met Phe Ala Arg Ser Asn Pro Pro Phe Asp
                245                 250                 255

Phe Phe Val Thr Ala Thr Gly Asp Thr Val Glu Met Ser Pro Phe Trp
            260                 265                 270

Ser Gly Glu Asp Asp His Glu Asn Lys Met His Glu Lys Pro Trp Phe
        275                 280                 285

Val Ser Val Ile Asn Asn Tyr Lys Val Val Asp Tyr Gln Asn Arg Gly
    290                 295                 300

Thr Val Pro Leu Gly Lys Thr Arg Ile Phe Leu Asp Arg Glu Glu Tyr
305                 310                 315                 320

Thr Leu Ser Trp Glu Lys His Leu Lys Asn Met Ser Tyr Cys Pro Leu
                325                 330                 335

Thr Leu Trp Lys Ala Phe Tyr Asn Gly Ile Gln Thr Glu His Ser Gly
            340                 345                 350

Ser Tyr His Phe Val Ala Asn Asp Ile Thr Ala Ser Phe Thr Thr Ser
        355                 360                 365

Lys Glu Asp Met Lys Glu Phe Asn Thr Thr Tyr His Cys Leu Asn Glu
    370                 375                 380

Glu Ile Lys Ala Glu Ile Glu Lys Lys Tyr Ala Lys Val Asn Ser Thr
385                 390                 395                 400

His Ser Lys Tyr Gly Asp Leu Lys Tyr Phe Lys Thr Asp Gly Gly Leu
                405                 410                 415

Tyr Leu Val Trp Gln Pro Leu Ile Gln Asn Arg Leu Leu Asp Ala Lys
            420                 425                 430

Asn Lys Leu Asn Asn Glu Thr Tyr Ser Arg Arg Ser Arg Arg Gln Ala
        435                 440                 445

Glu Ser Thr Thr Asp Pro Met Met Glu Met Thr Gly Asn Gly Ala Gly
    450                 455                 460

Gly Glu Tyr Ser Ser Glu Asn Ser Ile Thr Val Ala Gln Val Gln Tyr
465                 470                 475                 480

Ala Tyr Asp Asn Leu Arg Ile Arg Ile Asn Asn Ile Leu Glu Asp Leu
                485                 490                 495

Ser Lys Ala Trp Cys Arg Glu Gln His Arg Ala Ala Leu Val Trp Asn
            500                 505                 510

Glu Leu Ser Lys Ile Asn Pro Thr Ser Val Met Ser Met Ile Tyr Asn
        515                 520                 525

Arg Pro Val Ser Ala Lys Arg Ile Gly Asp Val Ile Ser Val Ser Asn
    530                 535                 540

Cys Ile Val Val Asp Gln Thr Ser Val Ser Leu His Lys Ser Leu Arg
545                 550                 555                 560

Leu Leu Ser Ala Ser Asp Glu Lys Cys Phe Ser Arg Pro Pro Val Thr
                565                 570                 575

Phe Lys Phe Met Asn Asp Ser Thr Ile Tyr Lys Gly Gln Leu Gly Val
```

-continued 580 585 590

Asn Asn Glu Ile Leu Leu Thr Thr Thr Tyr Leu Glu Thr Cys Gln Glu
595 600 605

Asn Thr Glu Tyr Tyr Phe Gln Ala Lys Thr Asp Met Tyr Ile Tyr Lys
610 615 620

Asn Tyr Glu His Leu Lys Thr Val Pro Leu Ser Ser Ile Thr Thr Leu
625 630 635 640

Asp Thr Phe Ile Ala Leu Asn Phe Thr Leu Leu Glu Asn Val Asp Phe
645 650 655

Lys Val Ile Glu Leu Tyr Thr Arg Asp Glu Lys Arg Leu Ser Asn Val
660 665 670

Phe Asp Ile Glu Thr Met Phe Arg Glu Tyr Asn Tyr Tyr Ala Gln Arg
675 680 685

Val Ser Gly Leu Arg Lys Asp Leu Leu Asp Leu Ser Thr Asn Arg Asn
690 695 700

Gln Phe Val Asp Ala Phe Gly Ser Leu Met Asp Asp Leu Gly Ala Val
705 710 715 720

Gly Gln Thr Val Val Asn Ala Val Ser Gly Val Ala Thr Leu Phe Ser
725 730 735

Ser Ile Val Thr Gly Phe Ile Asn Phe Ile Lys Asn Pro Phe Gly Gly
740 745 750

Met Leu Met Ile Ile Val Val Ile Gly Val Leu Phe Ala Ile Tyr Phe
755 760 765

Leu Thr Lys Lys Thr Lys Ile Tyr Glu Thr Ala Pro Ile Lys Met Ile
770 775 780

Tyr Pro Glu Ile Asp Lys Leu Lys Glu Arg Glu Gly Lys Ser Glu Ile
785 790 795 800

Ala Pro Ile Ser Glu Glu Glu Leu Glu Arg Ile Val Leu Ala Met His
805 810 815

Ile His Gln Gln Asn Ser His Met Glu Thr Lys Thr Arg Lys Asp Pro
820 825 830

Lys Asp Ser Ile Leu Thr Arg Ala Gln Asn Met Leu Arg Lys Arg Ser
835 840 845

Gly Tyr Ser Asn Leu Lys Asn Ala Glu Ser Val Glu Met Leu Asn Thr
850 855 860

Leu
865

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence:Sequencing primer for TOPO-pCRII: bases 434-458

<400> SEQUENCE: 25
cgccagggtt ttcccagtca cgac 24

<210> SEQ ID NO 26
<211> LENGTH: 17
<212> TYPE: DNA
<213> ORGANISM: Artificial Sequence
<220> FEATURE:
<223> OTHER INFORMATION: Description of Artificial Sequence:M13 reverse sequencing primer for TOPO-pCRII: bases 205-222

<400> SEQUENCE: 26

-continued caggaaacag ctatgac 17

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence:Sequencing primer for porcine gamma herpes virus gpB gene: base 1989-2008

<400> SEQUENCE: 27
cagggacgag aagaggctta 20

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence:Sequencing primer for porcine gamma herpes virus gpB gene: base 1513-1531

<400> SEQUENCE: 28
acaccagagc agctctatg 19

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence:Sequencing primer for porcine gamma herpes virus gpB gene: base 2399-2422

<400> SEQUENCE: 29
tagcaccaat cagtgaagaa gagc 24

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence:Sequencing primer for porcine gamma herpes virus gpB gene: base 322-343

<400> SEQUENCE: 30
gccagtgata tggtacacag tg 22

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence:Sequencing primer for porcine gamma herpes virus gpB gene: base 140-163

<400> SEQUENCE: 31
taacaggtca ctatggaaca cacg 24

<210> SEQ ID NO 32
<211> LENGTH: 24
<212> TYPE: DNA
<213> ORGANISM: Artificial Sequence
<220> FEATURE:

-continued

```
<223> OTHER INFORMATION: Description of Artificial Sequence:Sequencing
      primer for porcine gamma herpes virus gpB gene:
      base 537-560

<400> SEQUENCE: 32

ttctttaaga ctaaacacag gtgg                                          24


<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence:Sequencing
      primer for porcine gamma herpes virus gpB gene:
      base 815-835

<400> SEQUENCE: 33

ggagtggtga agatgatcat g                                             21


<210> SEQ ID NO 34
<211> LENGTH: 25
<212> TYPE: DNA
<213> ORGANISM: Artificial Sequence
<220> FEATURE:
<223> OTHER INFORMATION: Description of Artificial Sequence:Sequencing
      primer for porcine gamma herpes virus gpB gene:
      base 993-1017

<400> SEQUENCE: 34

ccataatgtt agtggacaat atgac                                         25


<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence:Sequencing
      primer for porcine gamma herpes virus gpB gene:
      base 1073-1093

<400> SEQUENCE: 35

atgacgctgt gatgtcattg g                                             21


<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence:Sequencing
      primer for porcine gamma herpes virus gpB gene:
      base 1673-1694

<400> SEQUENCE: 36

gatgcactga gaagcctgag ac                                            22
```